United States Patent
Huang et al.

(10) Patent No.: US 12,269,863 B2
(45) Date of Patent: Apr. 8, 2025

(54) BISPECIFIC T CELL ENGAGER AND USES THEREOF

(71) Applicant: MANYSMART THERAPEUTICS, INC., Tapei (TW)

(72) Inventors: Hsin-Yi Huang, Taipei (TW); Cheng Hao Liao, Taipei (TW); Chun-Ming Lin, Taipey (TW)

(73) Assignee: MANYSMART THERAPEUTICS, INC., Tapei (TW)

( * ) Notice: Subject to any disclaimer, the term of this patent is extended or adjusted under 35 U.S.C. 154(b) by 702 days.

(21) Appl. No.: 17/057,957

(22) PCT Filed: May 23, 2019

(86) PCT No.: PCT/US2019/033752
§ 371 (c)(1),
(2) Date: Nov. 23, 2020

(87) PCT Pub. No.: WO2019/226894
PCT Pub. Date: Nov. 28, 2019

(65) Prior Publication Data
US 2021/0261645 A1     Aug. 26, 2021

Related U.S. Application Data

(60) Provisional application No. 62/675,208, filed on May 23, 2018.

(51) Int. Cl.
| | |
|---|---|
| A61K 39/00 | (2006.01) |
| A61P 31/22 | (2006.01) |
| A61P 35/00 | (2006.01) |
| C07K 14/735 | (2006.01) |
| C07K 16/28 | (2006.01) |

(52) U.S. Cl.
CPC ........ C07K 14/70535 (2013.01); A61P 31/22 (2018.01); A61P 35/00 (2018.01); C07K 16/2809 (2013.01); A61K 2039/505 (2013.01); C07K 2317/622 (2013.01); C07K 2317/732 (2013.01); C07K 2319/02 (2013.01)

(58) Field of Classification Search
CPC .............................................. A61K 2039/505
See application file for complete search history.

(56) References Cited

U.S. PATENT DOCUMENTS

| | | | |
|---|---|---|---|
| 2004/0146889 A1 | 7/2004 | Dowdy et al. | |
| 2007/0207145 A1 | 9/2007 | Owens et al. | |
| 2011/0021729 A1 | 9/2011 | Birks et al. | |
| 2013/0078236 A1 | 3/2013 | Mary et al. | |
| 2015/0139943 A1 | 5/2015 | Campana et al. | |
| 2016/0227750 A1 | 8/2016 | Harada et al. | |
| 2017/0362299 A1* | 12/2017 | Li | C07K 14/70535 |
| 2018/0057795 A1 | 3/2018 | Childs et al. | |

FOREIGN PATENT DOCUMENTS

| | | | | |
|---|---|---|---|---|
| CN | 107108718 A | * | 8/2017 | ............ A61K 38/00 |
| JP | 2009-213430 A | | 9/2009 | |
| JP | 2013-529911 A | | 7/2013 | |
| JP | 2016-47 A | | 1/2016 | |
| JP | 2018-502068 A | | 1/2018 | |
| WO | WO-2006114700 A2 | * | 11/2006 | ............ C07K 16/00 |
| WO | 2007-041350 A2 | | 4/2007 | |
| WO | WO-2009158696 A1 | * | 12/2009 | ................ A61P 1/16 |
| WO | 2011-147981 A2 | | 12/2011 | |
| WO | WO-2012021648 A1 | * | 2/2012 | ............ G01N 33/53 |
| WO | 2016/094456 A1 | | 6/2016 | |
| WO | 2016/178996 A1 | | 11/2016 | |
| WO | 2015-056774 A1 | | 3/2017 | |
| WO | 2018027135 A1 | | 2/2018 | |
| WO | WO-2018022957 A1 | * | 2/2018 | ............ A61K 47/64 |

OTHER PUBLICATIONS

Lazar et al. (Molecular and Cellular Biology, 1988, 8: 1247-1252).*
Winkler et al. (J. Immunol. Oct. 15, 2000; 165 (8): 4505-4514).*
Caldas et al. (Mol. Immunol. May 2003; 39 (15): 941-952).*
Alegre et al. (Transplantation. Jun. 15, 1994; 57 (11): 1537-43).*
Herold et al. (Diabetes. Mar. 1992; 41 (3): 385-91).*
Perales-Puchalt et al. (JCI Insight. Apr. 18, 2019; 4 (8): e126086; pp. 1-8).*
Andrews et al. (Mol. Ther. Methods Clin. Dev. Sep. 20, 2017; 7: 74-82).*
Norris et al. (FEBS Open Bio. Apr. 25, 2018; 8 (6): 1029-42).*
Hölzer et al. (Cytokine. Mar. 1996; 8 (3): 214-21).*
Amet et al. (Pharm. Res. Mar. 2009; 26 (3): 523-8).*
Notice of Reasons for Rejection issued on corresponding Japanese application No. 2020-565337 dated Apr. 11, 2023.
ISR for International Application PCT/US2019/033752.
Written Opinion for International Application PCT/US2019/033752.
TW Office Action issued on Aug. 26, 2020 to the corresponding ROC (Taiwan) Patent Application No. 108117886.
TW Search Report issued on Aug. 26, 2020.
English translation to TW Search Report issued on Aug. 26, 2020.
Juan C. Almagro et al.: Progress and Challenges in the Design and Clinical Develop-ment of Antibodies for Cancer Therapy: Frontiers in Immunology: vol. 8: Article 1751 (2017).
Janakiraman Subramanian et al: Rituximab in the treatment of follicular lymphoma: the future of biosimilars in the evolving therapeutic landscape: Cancer Management and Research: 9: pp. 131-140: Apr. 24, 2017.
Niels W. C. J. van de Donk et al.: CD38 antibodies in multiple myeloma: back to the future: Blood Journal Organization: vol. 131: No. 1131: pp. 13-29: Jan. 4, 2018.

(Continued)

*Primary Examiner* — Stephen L Rawlings

(57) ABSTRACT

A novel fusion protein to overcome the current difficulties related to application of monoclonal antibodies in disease treatment and in other fields, particularly those requiring ADCC, e.g. for depletion of tumor cells, virally-infected cells, or immune-modulating cells, etc. One example of the fusion protein is an extracellular domain of a high-affinity variant of human CD16A fused to an anti-CD3 antibody or its antigen-binding fragment thereof that specifically binds to an epitope on human CD3 or a fragment thereof.

14 Claims, 15 Drawing Sheets

Specification includes a Sequence Listing.

(56) References Cited

OTHER PUBLICATIONS

K. Chin et al.: Avelumab: clinical trial innovation and collaboration to advance anti-PD-L1 immunotherapy: Annals of Oncology: vol. 28: Issue 7: 1658-1666: 2017.
Gerhard Hamilton et al.: Avelumab: combining immune checkpoint inhibition and antibody-dependent cytotoxicity: Expert Opinion on Biological Therapy: vol. 17: No. 4: pp. 515-523 (2017).
Masami Suzuki et al.: Therapeutic antibodies: their mechanisms of action and the pathological findings they induce in toxicity studies: J Toxicol Pathol, 28, 133-139 (2015).
Wolfgang Hiddemann et al.: Frontline therapy with rituximab added to the combination of cyclophosphamide, doxorubicin, vincristine, and prednisone (CHOP) significantly improves the outcome for patients with advanced-stage follicular lymphoma compared with therapy with CHOP alone: results of a prospective randomized study of the German Low-Grade Lymphoma: Blood, 106, 3725-32 (2005).
Laurie H. Sehn et al: Randomized Phase II Trial Comparing Obinutuzumab (GA101) With Rituximab in Patients With Relapsed CD20+Indolent B-Cell Non-Hodgkin Lymphoma: Final Analysis of the GAUSS Study: Journal of Clinical Oncology: vol. 33: No. 30: Oct. 20, 2015: pp. 3467-3474.
Wei Wang, et al: NK cell-mediated antibody dependent cellular cytotoxicity in cancer immunotherapy: Frontiers in Immunology: vol. 6: Article 368: Jul. 27, 2015: pp. 1-15.
Guillaume Cartron et al: Therapeutic activity of humanized anti-CD20 monoclonal antibody and polymorphism in IgG Fc receptor FcγRIIIa gene: Blood Journal: vol. 99: No. 3: Feb. 1, 2002: pp. 754-758.
Dong Hwan Kim et al: FCGR3A gene polymorphisms may correlate with response to frontline R-CHOP therapy for diffuse large B-cell lymphoma: Blood: vol. 108: No. 15: Oct. 2006: pp. 2720-2725.
Wu Zhang et al: FCGR2A and FCGR3A Polymorphisms Associated With Clinical Outcome of Epidermal Growth Factor Receptor—Expressing Metastatic Colorectal Cancer Patients Treated With Single-Agent Cetuximab: Journal of Clinical Oncology: vol. 25: No. 24: Aug. 20, 2007: pp. 3712-3718.
Antonino Musolino et al: Immunoglobulin G Fragment C Receptor Polymorphisms and Clinical Efficacy of Trastuzumab-Based Therapy in Patients With HER-2/neu—Positive Metastatic Breast Cancer: Journal of Clinical Oncology: vol. 26: No. 11: Apr. 10, 2008: pp. 1789-1796.
Suresh Veeramani et al: Rituximab infusion induces NK activation in lymphoma patients with the high-affinity CD16 polymorphism: Blood: vol. 118: No. 12: Sep. 22, 2011: pp. 3347-3349.
James Mellor et al: A critical review of the role of Fc gamma receptor polymorphisms in the response to monoclonal antibodies in cancer: Journal of Hematology & Oncology: 6:1: Jan. 4, 2013: pp. 1-10.
Drew M. Pardoll: The blockade of immune checkpoints in cancer immunotherapy: Nature Reviews | Cancer: vol. 12: Apr. 2012: pp. 252-264.
Suzanne L Topalian et al: Targeting the PD-1/B7-H1(PD-L1) pathway to activate anti-tumor immunity: SciVerse ScienceDirect: Current Opinion in Immunology: 24: 2012, pp. 207-212.
Michael A. Postow, et al: Immune Checkpoint Blockade in Cancer Therapy: Journal of Clinical Oncology: vol. 33: No. 17: Jun. 10, 2015: pp. 1974-1983.
Benjamin Boyerinas, et al: Antibody-Dependent Cellular Cytotoxicity Activity of a Novel Anti-PD-L1 Antibody Avelumab (MSB0010718C) on Human Tumor Cells: Cancer Immunology Research: 3(10): May 26, 2015: pp. 1148-1157.
Barton F. Haynes et al: Immune-Correlates Analysis of an HIV-1 Vaccine Efficacy Trial: The New England Journal of Medicine: vol. 366: No. 14: Apr. 5, 2012: pp. 1275-1286.
Matthew S. Parsons et al: Importance of Fc-mediated functions of anti-HIV-1 broadly neutralizing antibodies: Retrovirology: 15:58: 2018: pp. 1-12.
Shariq Mujib, et al: Comprehensive Cross-Clade Characterization of Antibody-Mediated Recognition, Complement-Mediated Lysis, and Cell-Mediated Cytotoxicity of HIV-1 Envelope-Specific Antibodies toward Eradication of the HIV-1 Reservoir: Journal of Virology: vol. 91: Issue 16: Aug. 2017: pp. 1-23.
Vijaya Madhavi et al: HIV-1 Env- and Vpu-Specific Antibody-Dependent Cellular Cytotoxicity Responses Associated with Elite Control of HIV: Journal of Virology—Pathogenesis and Immunity: vol. 91: Issue 18: Sep. 2017: pp. 1-16.
Ying Gao et al: Antibody-mediated immunotherapy against chronic hepatitis B virus infection: Human Vaccines & Immunotherapeutics: vol. 13: No. 8: 2017: pp. 1768-1773.
Anna E. Coghill et al: High Levels of Antibody that Neutralize B-cell Infection of Epstein-Barr Virus and that Bind EBV gp350 are Associated with a Lower Risk of Nasopharyngeal Carcinoma: Clinical Cancer Research: 22: Feb. 26, 2016: pp. 3451-3457.
Michael M. McVoy et al: A Native Human Monoclonal Antibody Targeting HCMV gB (AD-2 Site I): International Journal of Molecular Sciences: 19: 3982: Dec. 11, 2018: pp. 1-16.
Supplementary Search Report issued on Mar. 9, 2022 in European corresponding application No. 19806758.9.
Notice of First Examination Opinion issued on CN2019800347732 dated Mar. 26, 2024 (English Translation).
Notice of First Examination Opinion issued on CN2019800347732 dated Mar. 26, 2024 (Original in Mandarin).
Yang G.G. et al. Linker length affects expression and bioactivity of the onconase fusion protein in Pichia pastoris. Genet. Mol. Res. 14:19360-19370, 2015. (Supplement 1).
Guo H. et al. Effect of flexible linker length on the activity of fusion protein 4-coumaroyl-CoA ligase::stilbene synthase. Mol. BioSyst. DOI: 10.1039/c6mb00563b, 2017. (Supplement 2).
Zhao H.L. et al. Increasing the homogeneity, stability and activity of human serum albumin and interferon-a2b fusion protein by linker engineering. Protein Expression and Purification. 61:73-77, 2008. (Supplement 3).
Chen, X. et al. Fusion protein linkers: Property, design and functionality. Adv. Drug Deliv. Rev. doi.org/10.1016/j.addr.2012.09.039, 2012. (Supplement 4).

* cited by examiner

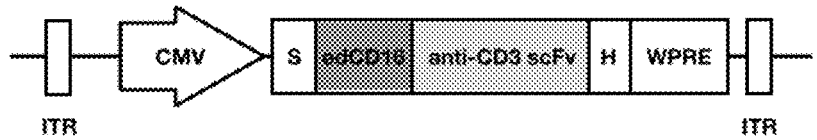

Figure 1A

1→ ATGGAGTGCAGCTGCGTGATGCTGTTCCTGCTGTCCGGAACCGCAGGCGTGCTGTCTAGGACA
GAGGACCTGCCAAAGGCCGTGGTGTTTCTGGAGCCCCAGTGGTACCGCGTGCTGGAGAAGGAC
TCCGTGACACTGAAGTGCCAGGGCGCCTATAGCCCTGAGGATAACTCCACCCAGTGGTTCCACA
ATGAGAGCCTGATCAGCTCCCAGGCCTCTAGCTACTTTATCGACGCAGCAACCGTGGACGATTCC
GGAGAGTATCGGTGCCAGACCAACCTGAGCACACTGTCCGATCCAGTGCAGCTGGAGGTGCAC
ATCGGATGGCTGCTGCTGCAGGCACCTAGATGGGTGTTCAAGGAGGAGGACCCCATCCACCTGC
GCTGTCACAGCTGGAAGAATACCGCCCTGCACAAGGTGACATACCTGCAGAACGGCAAGGGCC
GGAAGTACTTCCACCACAATTCTGACTTTTATATCCCCAAGGCCACACTGAAGGATAGCGGCTCCT
ATTTTTGCAGAGGCCTGGTGGGCAGCAAGAACGTGTCCTCTGAGACCGTGAATATCACCATCACA
CAGGGACTGGCACAGGTGCAGCTGCAGCAGAGCGGAGCAGAGCTGGCAAGGCCTGGAGCCTC
CGTGAAGATGTCTTGTAAGGCCAGCGGCTACACCTTCACACGGTATACAATGCACTGGGTGAAGC
AGAGACCAGGACAGGGACTGGAGTGGATCGGATACATCAACCCTTCCCGCGGCTACACCAACTA
TAATCAGAAGTTTAAGGACAAGGCCACCCTGACCACAGATAAGAGCTCCTCTACAGCCTACATGC
AGCTGAGCTCCCTGACCTCTGAGGACAGCGCCGTGTACTATTGCGCCAGATACTATGACGATCAC
TACTGTCTGGATTATTGGGGCCAGGGCACCACACTGACAGTGTCTAGCGTGGAGGGAGGCTCCG
GAGGCTCTGGAGGCAGCGGCGGCTCCGGAGGAGTGGACCAGATCGTGCTGACCCAGTCCCCA
GCAATCATGTCTGCCAGCCCTGGAGAGAAGGTGACCATGACATGCTCTGCCTCCTCTAGCGTGA
GCTACATGAATTGGTATCAGCAGAAGTCTGGCACAAGCCCAAAGCGGTGGATCTACGACACCTCC
AAGCTGGCATCTGGAGTGCCAGCACACTTCAGAGGCTCTGGCAGCGGCACCTCCTATTCTCTGA
CAATCTCCGGAATGGAGGCAGAGGATGCAGCAACCTACTATTGTCAGCAGTGGTCCTCTAACCCC
TTCACCTTTGGCTCTGGCACAAAGCTGGAGATCAATAGACATCACCACCACCACCACTGA ←1341

Figure 1B

1→ MECSCVMLFLLSGTAGVLSRTEDLPKAVVFLEPQWYRVLEKDSVTLKCQGAYSPEDNSTQWFHNESL
ISSQASSYFIDAATVDDSGEYRCQTNLSTLSDPVQLEVHIGWLLLQAPRWVFKEEDPIHLRCHSWKNT
ALHKVTYLQNGKGRKYFHHNSDFYIPKATLKDSGSYFCRGLVGSKNVSSETVNITITQGLAQVQLQQS
GAELARPGASVKMSCKASGYTFTRYTMHWVKQRPGQGLEWIGYINPSRGYTNYNQKFKDKATLTTD
KSSSTAYMQLSSLTSEDSAVYYCARYYDDHYCLDYWGQGTTLTVSSVEGGSGGSGGSGGSGGVDQI
VLTQSPAIMSASPGEKVTMTCSASSSVSYMNWYQQKSGTSPKRWIYDTSKLASGVPAHFRGSGSGT
SYSLTISGMEAEDAATYYCQQWSSNPFTFGSGTKLEINRHHHHHH ←446

Figure 1C

```
Start (0)
ATGGAGTGCAGCTGCGTGATGCTGTTCCTGCTGTCCGGAACCGCAGGCGTGCTGTCTAGG
||||||||||||||||||||||||||||||||||||||||||||||||||||||||||||   60
TACCTCACGTCGACGCACTACGACAAGGACGACAGGCCTTGGCGTCCGCACGACAGATCC
         5         10        15         1
 M  E  C  S  V  M  L  F  L  L  S  G  T  A  G  V  L  S  R
 ═════════════ secretion signal ═══════════════════ >
                                        CD16a extracellular (edCD16)
         5         10        15        20
 M  E  C  S  V  M  L  F  L  L  S  G  T  A  G  V  L  S  R
 ═══════════════════ CD16A-BiTE ═════════════════════ >

ACAGAGGACCTGCCAAAGGCCGTGGTGTTTCTGGAGCCCCAGTGGTACCGCGTGCTGGAG
||||||||||||||||||||||||||||||||||||||||||||||||||||||||||||   120
TGTCTCCTGGACGGTTTCCGGCACCACAAAGACCTCGGGGTCACCATGGCGCACGACCTC
         5         10        15        20
 T  E  D  L  P  K  A  V  V  F  L  E  P  Q  W  Y  R  V  L  E
 ═════════ CD16A extracellular domain (edCD16) ══════ >
           25        30        35        40
 T  E  D  L  P  K  A  V  V  F  L  E  P  Q  W  Y  R  V  L  E
 ═══════════════════ CD16A-BiTE ═════════════════════ >

AAGGACTCCGTGACACTGAAGTGCCAGGGCGCCTATAGCCCTGAGGATAACTCCACCCAG
||||||||||||||||||||||||||||||||||||||||||||||||||||||||||||   180
TTCCTGAGGCACTGTGACTTCACGGTCCCGCGGATATCGGGACTCCTATTGAGGTGGGTC
          25        30        35        40
 K  D  S  V  T  L  K  C  Q  G  A  Y  S  P  E  D  N  S  T  Q
 ═════════ CD16A extracellular domain (edCD16) ══════ >
           45        50        55        60
 K  D  S  V  T  L  K  C  Q  G  A  Y  S  P  E  D  N  S  T  Q
 ═══════════════════ CD16A-BiTE ═════════════════════ >

TGGTTCCACAATGAGAGCCTGATCAGCTCCCAGGCCTCTAGCTACTTTATCGACGCAGCA
||||||||||||||||||||||||||||||||||||||||||||||||||||||||||||   240
ACCAAGGTGTTACTCTCGGACTAGTCGAGGGTCCGGAGATCGATGAAATAGCTGCGTCGT
          45        50        55        60
 W  F  H  N  E  S  L  I  S  S  Q  A  S  S  Y  F  I  D  A  A
 ═════════ CD16A extracellular domain (edCD16) ══════ >
           65        70        75        80
 W  F  H  N  E  S  L  I  S  S  Q  A  S  S  Y  F  I  D  A  A
 ═══════════════════ CD16A-BiTE ═════════════════════ >

ACCGTGGACGATTCCGGAGAGTATCGGTGCCAGACCAACCTGAGCACACTGTCCGATCCA
||||||||||||||||||||||||||||||||||||||||||||||||||||||||||||   300
TGGCACCTGCTAAGGCCTCTCATAGCCACGGTCTGGTTGGACTCGTGTGACAGGCTAGGT
          65        70        75        80
 T  V  D  D  S  G  E  Y  R  C  Q  T  N  L  S  T  L  S  D  P
 ═════════ CD16A extracellular domain (edCD16) ══════ >
           85        90        95       100
 T  V  D  D  S  G  E  Y  R  C  Q  T  N  L  S  T  L  S  D  P
 ═══════════════════ CD16A-BiTE ═════════════════════ >
```

Line: isotype antibody

Shadow: anti-CD20/anti-EGFR

Line: without IgG antibody

Shadow: with IgG antibody

SEQUENCE LISTING

```
<160> NUMBER OF SEQ ID NOS: 8

<210> SEQ ID NO 1
<211> LENGTH: 531
<212> TYPE: DNA
<213> ORGANISM: Homo sapiens
<220> FEATURE:
<221> NAME/KEY: CDS
<222> LOCATION: (1)..(531)

<400> SEQUENCE: 1 agg aca gag gac ctg cca aag gcc gtg gtg ttt ctg gag ccc cag tgg      48
Arg Thr Glu Asp Leu Pro Lys Ala Val Val Phe Leu Glu Pro Gln Trp
1               5                   10                  15 tac cgc gtg ctg gag aag gac tcc gtg aca ctg aag tgc cag ggc gcc      96
Tyr Arg Val Leu Glu Lys Asp Ser Val Thr Leu Lys Cys Gln Gly Ala
                20                  25                  30 tat agc cct gag gat aac tcc acc cag tgg ttc cac aat gag agc ctg     144
Tyr Ser Pro Glu Asp Asn Ser Thr Gln Trp Phe His Asn Glu Ser Leu
            35                  40                  45 atc agc tcc cag gcc tct agc tac ttt atc gac gca gca acc gtg gac     192
Ile Ser Ser Gln Ala Ser Ser Tyr Phe Ile Asp Ala Ala Thr Val Asp
        50                  55                  60 gat tcc gga gag tat cgg tgc cag acc aac ctg agc aca ctg tcc gat     240
Asp Ser Gly Glu Tyr Arg Cys Gln Thr Asn Leu Ser Thr Leu Ser Asp
65                  70                  75                  80 cca gtg cag ctg gag gtg cac atc gga tgg ctg ctg ctg cag gca cct     288
Pro Val Gln Leu Glu Val His Ile Gly Trp Leu Leu Leu Gln Ala Pro
                85                  90                  95 aga tgg gtg ttc aag gag gag gac ccc atc cac ctg cgc tgt cac agc     336
Arg Trp Val Phe Lys Glu Glu Asp Pro Ile His Leu Arg Cys His Ser
                100                 105                 110 tgg aag aat acc gcc ctg cac aag gtg aca tac ctg cag aac ggc aag     384
```

```
Trp Lys Asn Thr Ala Leu His Lys Val Thr Tyr Leu Gln Asn Gly Lys
            115                 120                 125 ggc cgg aag tac ttc cac cac aat tct gac ttt tat atc ccc aag gcc      432
Gly Arg Lys Tyr Phe His His Asn Ser Asp Phe Tyr Ile Pro Lys Ala
        130                 135                 140 aca ctg aag gat agc ggc tcc tat ttt tgc aga ggc ctg gtg ggc agc      480
Thr Leu Lys Asp Ser Gly Ser Tyr Phe Cys Arg Gly Leu Val Gly Ser
145                 150                 155                 160 aag aac gtg tcc tct gag acc gtg aat atc acc atc aca cag gga ctg      528
Lys Asn Val Ser Ser Glu Thr Val Asn Ile Thr Ile Thr Gln Gly Leu
                165                 170                 175 gca                                                                  531
Ala

<210> SEQ ID NO 2
<211> LENGTH: 177
<212> TYPE: PRT
<213> ORGANISM: Homo sapiens

<400> SEQUENCE: 2

Arg Thr Glu Asp Leu Pro Lys Ala Val Val Phe Leu Glu Pro Gln Trp
1               5                   10                  15

Tyr Arg Val Leu Glu Lys Asp Ser Val Thr Leu Lys Cys Gln Gly Ala
            20                  25                  30

Tyr Ser Pro Glu Asp Asn Ser Thr Gln Trp Phe His Asn Glu Ser Leu
        35                  40                  45

Ile Ser Ser Gln Ala Ser Ser Tyr Phe Ile Asp Ala Ala Thr Val Asp
    50                  55                  60

Asp Ser Gly Glu Tyr Arg Cys Gln Thr Asn Leu Ser Thr Leu Ser Asp
65                  70                  75                  80

Pro Val Gln Leu Glu Val His Ile Gly Trp Leu Leu Leu Gln Ala Pro
                85                  90                  95

Arg Trp Val Phe Lys Glu Glu Asp Pro Ile His Leu Arg Cys His Ser
            100                 105                 110

Trp Lys Asn Thr Ala Leu His Lys Val Thr Tyr Leu Gln Asn Gly Lys
        115                 120                 125

Gly Arg Lys Tyr Phe His His Asn Ser Asp Phe Tyr Ile Pro Lys Ala
    130                 135                 140

Thr Leu Lys Asp Ser Gly Ser Tyr Phe Cys Arg Gly Leu Val Gly Ser
145                 150                 155                 160

Lys Asn Val Ser Ser Glu Thr Val Asn Ile Thr Ile Thr Gln Gly Leu
                165                 170                 175

Ala

<210> SEQ ID NO 3
<211> LENGTH: 732
<212> TYPE: DNA
<213> ORGANISM: Artificial Sequence
<220> FEATURE:
<223> OTHER INFORMATION: scFv
<220> FEATURE:
<221> NAME/KEY: CDS
<222> LOCATION: (1)..(732)

<400> SEQUENCE: 3 cag gtg cag ctg cag cag agc gga gca gag ctg gca agg cct gga gcc       48
Gln Val Gln Leu Gln Gln Ser Gly Ala Glu Leu Ala Arg Pro Gly Ala
1               5                   10                  15 tcc gtg aag atg tct tgt aag gcc agc ggc tac acc ttc aca cgg tat       96
```

```
Ser Val Lys Met Ser Cys Lys Ala Ser Gly Tyr Thr Phe Thr Arg Tyr
             20                  25                  30 aca atg cac tgg gtg aag cag aga cca gga cag gga ctg gag tgg atc        144
Thr Met His Trp Val Lys Gln Arg Pro Gly Gln Gly Leu Glu Trp Ile
         35                  40                  45 gga tac atc aac cct tcc cgc ggc tac acc aac tat aat cag aag ttt        192
Gly Tyr Ile Asn Pro Ser Arg Gly Tyr Thr Asn Tyr Asn Gln Lys Phe
 50                  55                  60 aag gac aag gcc acc ctg acc aca gat aag agc tct tct aca gcc tac        240
Lys Asp Lys Ala Thr Leu Thr Thr Asp Lys Ser Ser Ser Thr Ala Tyr
 65                  70                  75                  80 atg cag ctg agc tcc ctg acc tct gag gac agc gcc gtg tac tat tgc        288
Met Gln Leu Ser Ser Leu Thr Ser Glu Asp Ser Ala Val Tyr Tyr Cys
             85                  90                  95 gcc aga tac tat gac gat cac tac tgt ctg gat tat tgg ggc cag ggc        336
Ala Arg Tyr Tyr Asp Asp His Tyr Cys Leu Asp Tyr Trp Gly Gln Gly
            100                 105                 110 acc aca ctg aca gtg tct agc gtg gag gga ggc tcc gga ggc tct gga        384
Thr Thr Leu Thr Val Ser Ser Val Glu Gly Gly Ser Gly Gly Ser Gly
            115                 120                 125 ggc agc ggc ggc tcc gga gga gtg gac cag atc gtg ctg acc cag tcc        432
Gly Ser Gly Gly Ser Gly Gly Val Asp Gln Ile Val Leu Thr Gln Ser
130                 135                 140 cca gca atc atg tct gcc agc cct gga gag aag gtg acc atg aca tgc        480
Pro Ala Ile Met Ser Ala Ser Pro Gly Glu Lys Val Thr Met Thr Cys
145                 150                 155                 160 tct gcc tcc tct agc gtg agc tac atg aat tgg tat cag cag aag tct        528
Ser Ala Ser Ser Ser Val Ser Tyr Met Asn Trp Tyr Gln Gln Lys Ser
                165                 170                 175 ggc aca agc cca aag cgg tgg atc tac gac acc tcc aag ctg gca tct        576
Gly Thr Ser Pro Lys Arg Trp Ile Tyr Asp Thr Ser Lys Leu Ala Ser
            180                 185                 190 gga gtg cca gca cac ttc aga ggc tct ggc agc ggc acc tcc tat tct        624
Gly Val Pro Ala His Phe Arg Gly Ser Gly Ser Gly Thr Ser Tyr Ser
            195                 200                 205 ctg aca atc tcc gga atg gag gca gag gat gca gca acc tac tat tgt        672
Leu Thr Ile Ser Gly Met Glu Ala Glu Asp Ala Ala Thr Tyr Tyr Cys
210                 215                 220 cag cag tgg tcc tct aac ccc ttc acc ttt ggc tct ggc aca aag ctg        720
Gln Gln Trp Ser Ser Asn Pro Phe Thr Phe Gly Ser Gly Thr Lys Leu
225                 230                 235                 240 gag atc aat aga                                                        732
Glu Ile Asn Arg <210> SEQ ID NO 4
<211> LENGTH: 244
<212> TYPE: PRT
<213> ORGANISM: Artificial Sequence
<220> FEATURE:
<223> OTHER INFORMATION: Synthetic Construct

<400> SEQUENCE: 4

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
             20                  25                  30

Thr Met His Trp Val Lys Gln Arg Pro Gly Gln Gly Leu Glu Trp Ile
         35                  40                  45

Gly Tyr Ile Asn Pro Ser Arg Gly Tyr Thr Asn Tyr Asn Gln Lys Phe
 50                  55                  60
```

```
Lys Asp Lys Ala Thr Leu Thr Thr Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Val Asp Gln Ile Val Leu Thr Gln Ser
    130                 135                 140

Pro Ala Ile Met Ser Ala Ser Pro Gly Glu Lys Val Thr Met Thr Cys
145                 150                 155                 160

Ser Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Leu Ala Ser
            180                 185                 190

Gly Val Pro Ala His Phe Arg Gly Ser Gly Ser Gly Thr Ser Tyr Ser
        195                 200                 205

Leu Thr Ile Ser Gly Met Glu Ala Glu Asp Ala Ala Thr Tyr Tyr Cys
    210                 215                 220

Gln Gln Trp Ser Ser Asn Pro Phe Thr Phe Gly Ser Gly Thr Lys Leu
225                 230                 235                 240

Glu Ile Asn Arg

<210> SEQ ID NO 5
<211> LENGTH: 57
<212> TYPE: DNA
<213> ORGANISM: Artificial Sequence
<220> FEATURE:
<223> OTHER INFORMATION: secretion signal
<220> FEATURE:
<221> NAME/KEY: CDS
<222> LOCATION: (1)..(57)

<400> SEQUENCE: 5 atg gag tgc agc tgc gtg atg ctg ttc ctg ctg tcc gga acc gca ggc    48
Met Glu Cys Ser Cys Val Met Leu Phe Leu Leu Ser Gly Thr Ala Gly
  1               5                  10                  15 gtg ctg tct                                                        57
Val Leu Ser <210> SEQ ID NO 6
<211> LENGTH: 19
<212> TYPE: PRT
<213> ORGANISM: Artificial Sequence
<220> FEATURE:
<223> OTHER INFORMATION: Synthetic Construct

<400> SEQUENCE: 6

Met Glu Cys Ser Cys Val Met Leu Phe Leu Leu Ser Gly Thr Ala Gly
  1               5                  10                  15

Val Leu Ser

<210> SEQ ID NO 7
<211> LENGTH: 1341
<212> TYPE: DNA
<213> ORGANISM: Artificial Sequence
<220> FEATURE:
<223> OTHER INFORMATION: Fusion protein
<220> FEATURE:
```

<221> NAME/KEY: CDS
<222> LOCATION: (1)..(1338)

<400> SEQUENCE: 7

```
atg gag tgc agc tgc gtg atg ctg ttc ctg ctg tcc gga acc gca ggc      48
Met Glu Cys Ser Cys Val Met Leu Phe Leu Leu Ser Gly Thr Ala Gly
 1               5                  10                  15 gtg ctg tct agg aca gag gac ctg cca aag gcc gtg gtg ttt ctg gag      96
Val Leu Ser Arg Thr Glu Asp Leu Pro Lys Ala Val Val Phe Leu Glu
             20                  25                  30 ccc cag tgg tac cgc gtg ctg gag aag gac tcc gtg aca ctg aag tgc     144
Pro Gln Trp Tyr Arg Val Leu Glu Lys Asp Ser Val Thr Leu Lys Cys
         35                  40                  45 cag ggc gcc tat agc cct gag gat aac tcc acc cag tgg ttc cac aat     192
Gln Gly Ala Tyr Ser Pro Glu Asp Asn Ser Thr Gln Trp Phe His Asn
     50                  55                  60 gag agc ctg atc agc tcc cag gcc tct agc tac ttt atc gac gca gca     240
Glu Ser Leu Ile Ser Ser Gln Ala Ser Ser Tyr Phe Ile Asp Ala Ala
 65                  70                  75                  80 acc gtg gac gat tcc gga gag tat cgg tgc cag acc aac ctg agc aca     288
Thr Val Asp Asp Ser Gly Glu Tyr Arg Cys Gln Thr Asn Leu Ser Thr
                 85                  90                  95 ctg tcc gat cca gtg cag ctg gag gtg cac atc gga tgg ctg ctg ctg     336
Leu Ser Asp Pro Val Gln Leu Glu Val His Ile Gly Trp Leu Leu Leu
            100                 105                 110 cag gca cct aga tgg gtg ttc aag gag gag gac ccc atc cac ctg cgc     384
Gln Ala Pro Arg Trp Val Phe Lys Glu Glu Asp Pro Ile His Leu Arg
        115                 120                 125 tgt cac agc tgg aag aat acc gcc ctg cac aag gtg aca tac ctg cag     432
Cys His Ser Trp Lys Asn Thr Ala Leu His Lys Val Thr Tyr Leu Gln
    130                 135                 140 aac ggc aag ggc cgg aag tac ttc cac cac aat tct gac ttt tat atc     480
Asn Gly Lys Gly Arg Lys Tyr Phe His His Asn Ser Asp Phe Tyr Ile
145                 150                 155                 160 ccc aag gcc aca ctg aag gat agc ggc tcc tat ttt tgc aga ggc ctg     528
Pro Lys Ala Thr Leu Lys Asp Ser Gly Ser Tyr Phe Cys Arg Gly Leu
                165                 170                 175 gtg ggc agc aag aac gtg tcc tct gag acc gtg aat atc acc atc aca     576
Val Gly Ser Lys Asn Val Ser Ser Glu Thr Val Asn Ile Thr Ile Thr
            180                 185                 190 cag gga ctg gca cag gtg cag ctg cag cag agc gga gca gag ctg gca     624
Gln Gly Leu Ala Gln Val Gln Leu Gln Gln Ser Gly Ala Glu Leu Ala
        195                 200                 205 agg cct gga gcc tcc gtg aag atg tct tgt aag gcc agc ggc tac acc     672
Arg Pro Gly Ala Ser Val Lys Met Ser Cys Lys Ala Ser Gly Tyr Thr
    210                 215                 220 ttc aca cgg tat aca atg cac tgg gtg aag cag aga cca gga cag gga     720
Phe Thr Arg Tyr Thr Met His Trp Val Lys Gln Arg Pro Gly Gln Gly
225                 230                 235                 240 ctg gag tgg atc gga tac atc aac cct tcc cgc ggc tac acc aac tat     768
Leu Glu Trp Ile Gly Tyr Ile Asn Pro Ser Arg Gly Tyr Thr Asn Tyr
                245                 250                 255 aat cag aag ttt aag gac aag gcc acc ctg acc aca gat aag agc tcc     816
Asn Gln Lys Phe Lys Asp Lys Ala Thr Leu Thr Thr Asp Lys Ser Ser
            260                 265                 270 tct aca gcc tac atg cag ctg agc tcc ctg acc tct gag gac agc gcc     864
Ser Thr Ala Tyr Met Gln Leu Ser Ser Leu Thr Ser Glu Asp Ser Ala
        275                 280                 285 gtg tac tat tgc gcc aga tac tat gac gat cac tac tgt ctg gat tat     912
Val Tyr Tyr Cys Ala Arg Tyr Tyr Asp Asp His Tyr Cys Leu Asp Tyr
```

```
                    290                 295                 300
tgg ggc cag ggc acc aca ctg aca gtg tct agc gtg gag gga ggc tcc      960
Trp Gly Gln Gly Thr Thr Leu Thr Val Ser Ser Val Glu Gly Gly Ser
305                 310                 315                 320 gga ggc tct gga ggc agc ggc ggc tcc gga gga gtg gac cag atc gtg     1008
Gly Gly Ser Gly Gly Ser Gly Gly Ser Gly Gly Val Asp Gln Ile Val
                325                 330                 335 ctg acc cag tcc cca gca atc atg tct gcc agc cct gga gag aag gtg     1056
Leu Thr Gln Ser Pro Ala Ile Met Ser Ala Ser Pro Gly Glu Lys Val
                340                 345                 350 acc atg aca tgc tct gcc tcc tct agc gtg agc tac atg aat tgg tat     1104
Thr Met Thr Cys Ser Ala Ser Ser Ser Val Ser Tyr Met Asn Trp Tyr
                355                 360                 365 cag cag aag tct gga aca agc cca aag cgg tgg atc tac gac acc tcc     1152
Gln Gln Lys Ser Gly Thr Ser Pro Lys Arg Trp Ile Tyr Asp Thr Ser
370                 375                 380 aag ctg gca tct gga gtg cca gca cac ttc aga ggc tct ggc agc ggc     1200
Lys Leu Ala Ser Gly Val Pro Ala His Phe Arg Gly Ser Gly Ser Gly
385                 390                 395                 400 acc tcc tat tct ctg aca atc tcc gga atg gag gca gag gat gca gca     1248
Thr Ser Tyr Ser Leu Thr Ile Ser Gly Met Glu Ala Glu Asp Ala Ala
                405                 410                 415 acc tac tat tgt cag cag tgg tcc tct aac ccc ttc acc ttt ggc tct     1296
Thr Tyr Tyr Cys Gln Gln Trp Ser Ser Asn Pro Phe Thr Phe Gly Ser
                420                 425                 430 ggc aca aag ctg gag atc aat aga cat cac cac cac cac cac tga         1341
Gly Thr Lys Leu Glu Ile Asn Arg His His His His His His
                435                 440                 445

<210> SEQ ID NO 8
<211> LENGTH: 446
<212> TYPE: PRT
<213> ORGANISM: Artificial Sequence
<220> FEATURE:
<223> OTHER INFORMATION: Synthetic Construct

<400> SEQUENCE: 8

Met Glu Cys Ser Cys Val Met Leu Phe Leu Leu Ser Gly Thr Ala Gly
1               5                   10                  15

Val Leu Ser Arg Thr Glu Asp Leu Pro Lys Ala Val Val Phe Leu Glu
                20                  25                  30

Pro Gln Trp Tyr Arg Val Leu Glu Lys Asp Ser Val Thr Leu Lys Cys
            35                  40                  45

Gln Gly Ala Tyr Ser Pro Glu Asp Asn Ser Thr Gln Trp Phe His Asn
        50                  55                  60

Glu Ser Leu Ile Ser Ser Gln Ala Ser Ser Tyr Phe Ile Asp Ala Ala
65                  70                  75                  80

Thr Val Asp Asp Ser Gly Glu Tyr Arg Cys Gln Thr Asn Leu Ser Thr
                85                  90                  95

Leu Ser Asp Pro Val Gln Leu Glu Val His Ile Gly Trp Leu Leu Leu
                100                 105                 110

Gln Ala Pro Arg Trp Val Phe Lys Glu Glu Asp Pro Ile His Leu Arg
            115                 120                 125

Cys His Ser Trp Lys Asn Thr Ala Leu His Lys Val Thr Tyr Leu Gln
        130                 135                 140

Asn Gly Lys Gly Arg Lys Tyr Phe His His Asn Ser Asp Phe Tyr Ile
145                 150                 155                 160

Pro Lys Ala Thr Leu Lys Asp Ser Gly Ser Tyr Phe Cys Arg Gly Leu
```

-continued

```
            165                 170                 175
Val Gly Ser Lys Asn Val Ser Ser Glu Thr Val Asn Ile Thr Ile Thr
            180                 185                 190

Gln Gly Leu Ala Gln Val Gln Leu Gln Gln Ser Gly Ala Glu Leu Ala
            195                 200                 205

Arg Pro Gly Ala Ser Val Lys Met Ser Cys Lys Ala Ser Gly Tyr Thr
            210                 215                 220

Phe Thr Arg Tyr Thr Met His Trp Val Lys Gln Arg Pro Gly Gln Gly
225                 230                 235                 240

Leu Glu Trp Ile Gly Tyr Ile Asn Pro Ser Arg Gly Tyr Thr Asn Tyr
            245                 250                 255

Asn Gln Lys Phe Lys Asp Lys Ala Thr Leu Thr Thr Asp Lys Ser Ser
            260                 265                 270

Ser Thr Ala Tyr Met Gln Leu Ser Ser Leu Thr Ser Glu Asp Ser Ala
            275                 280                 285

Val Tyr Tyr Cys Ala Arg Tyr Tyr Asp Asp His Tyr Cys Leu Asp Tyr
            290                 295                 300

Trp Gly Gln Gly Thr Thr Leu Thr Val Ser Ser Val Glu Gly Gly Ser
305                 310                 315                 320

Gly Gly Ser Gly Gly Ser Gly Gly Ser Gly Gly Val Asp Gln Ile Val
            325                 330                 335

Leu Thr Gln Ser Pro Ala Ile Met Ser Ala Ser Pro Gly Glu Lys Val
            340                 345                 350

Thr Met Thr Cys Ser Ala Ser Ser Val Ser Tyr Met Asn Trp Tyr
            355                 360                 365

Gln Gln Lys Ser Gly Thr Ser Pro Lys Arg Trp Ile Tyr Asp Thr Ser
            370                 375                 380

Lys Leu Ala Ser Gly Val Pro Ala His Phe Arg Gly Ser Gly Ser Gly
385                 390                 395                 400

Thr Ser Tyr Ser Leu Thr Ile Ser Gly Met Glu Ala Glu Asp Ala Ala
            405                 410                 415

Thr Tyr Tyr Cys Gln Gln Trp Ser Ser Asn Pro Phe Thr Phe Gly Ser
            420                 425                 430

Gly Thr Lys Leu Glu Ile Asn Arg His His His His His
            435                 440                 445
```

BISPECIFIC T CELL ENGAGER AND USES THEREOF

This application is a national phase entry under 35 USC 371 of International Patent Application No.: PCT/US2019/033752 filed on 23 May 2019, which claims the benefit of U.S. Provisional Patent Application No. 62/675,208, filed on 23 May 2018, the entire content of which is incorporated by reference.

FIELD OF THE INVENTION

The present disclosure relates to a fusion protein, particularly, to a CD16A-bispecific T cell engager (BITE®) and uses thereof.

BACKGROUND OF THE INVENTION

Therapeutic monoclonal antibodies (mAbs) have become one of the fastest growing classes of drugs in recent years and are approved for the treatment of a wide range of indications, from cancer, infectious disease, and to autoimmune disease (Almagro et al., Front Immunol 8, 1751 (2017)). The majority of mAbs approved for use in oncology are the so-called direct-targeting mAbs, such as rituximab (an anti-CD20 mAb), which are designed to target tumor cells directly. This type of mAb is usually made ex vivo and passively injected into patients, where they act against established or residual tumors and thereby activate various Fc-receptor-mediated effector pathways to kill the target cells. When combined with chemotherapy, these is therapeutic mAbs have achieved impressive results for hematologic malignancies, with anti-CD20 and anti-CD38 as examples of clinical efficacy in follicular lymphoma (Subramanian et al., Cancer Management and Research, 9, 131-140 (2017)) and multiple myeloma (van de Donk et al., Blood, 131, 13-29 (2018)), respectively. Instead, approved immunomodulatory mAbs, such as anti-CTLA-4 (Cytotoxic T-lymphocyte antigen 4), anti-PD-1 (Programmed Cell Death-1), and anti-PD-L1 (Programmed Death-Ligand1) are designed to block immune checkpoint to reactivate antitumor immune responses (K. Chin et al., Annals of Oncology, 28, 1658-1666 (2017)), but may also function as direct-targeting mAbs to delete cells (Hamilton and Rath Expert Opinion on Biological Therapy, 17, 515-523 (2017)).

The mechanism of action of direct-targeting therapeutic mAbs stems from various natural functions of antibodies: neutralization, antibody-dependent cell-mediated cytotoxicity (ADCC), or complement-dependent cytotoxicity (Suzuki et al., J Toxicol Pathol, 28, 133-139 (2015)). The extent to which each mode of action contributes to clinical efficacy is unclear.

Therefore, there is need for developing a novel approach to improve therapeutic efficacy of mAbs and to boost mAb application in various fields. The present disclosure addressed these and other needs.

SUMMARY OF THE INVENTION

The present disclosure provides a novel bispecific T cell engager to overcome the current difficulties related to application of mAbs in disease treatment and in other fields, particularly those requiring ADCC, e.g. depletion of tumor cells, virally-infected cells, or immune-modulating cells, etc.

The present disclosure provides a fusion protein comprising:
an extracellular domain of human CD16A; and
an antibody or antigen-binding fragment thereof that specifically binds to an epitope on human CD3 or a fragment thereof.

The present disclosure also provides a polynucleotide encoding the fusion protein as disclosed herein.

The present disclosure also provides a host cell comprising the polynucleotide as disclosed herein.

The present disclosure also provides a pharmaceutical composition comprising a therapeutically effective amount of the fusion protein as disclosed herein and optionally a pharmaceutically acceptable carrier or excipient.

The present disclosure also provides use of the pharmaceutical composition as disclosed herein in the manufacture of a medicament for inducing antibody-dependent cellular cytotoxicity in a subject in need.

The present disclosure is described in detail in the following sections. Other characteristics, purposes and advantages of the present disclosure can be found in the detailed description and claims.

BRIEF DESCRIPTION OF THE DRAWINGS

Figure 1E:
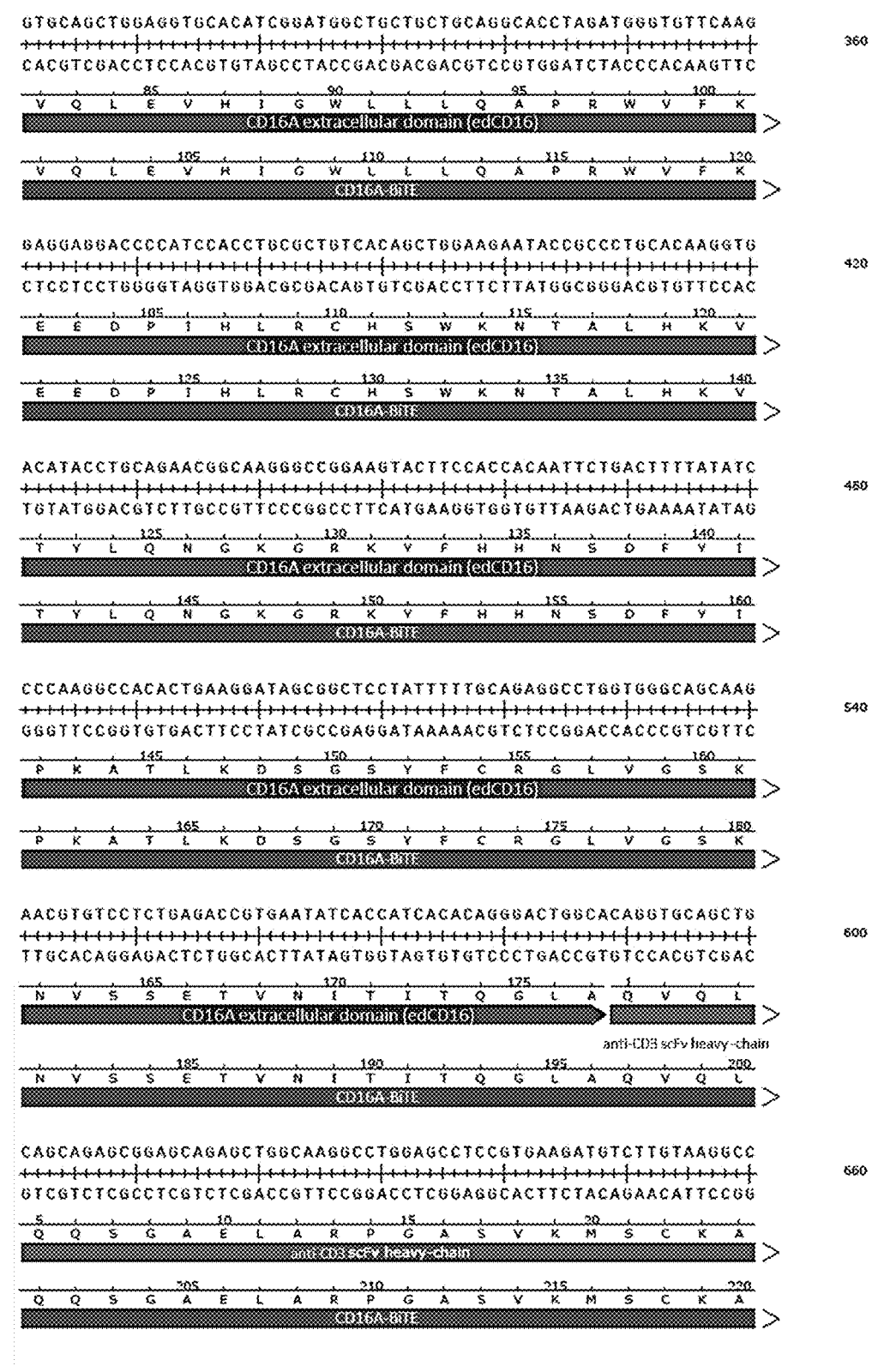
Figure 1F:
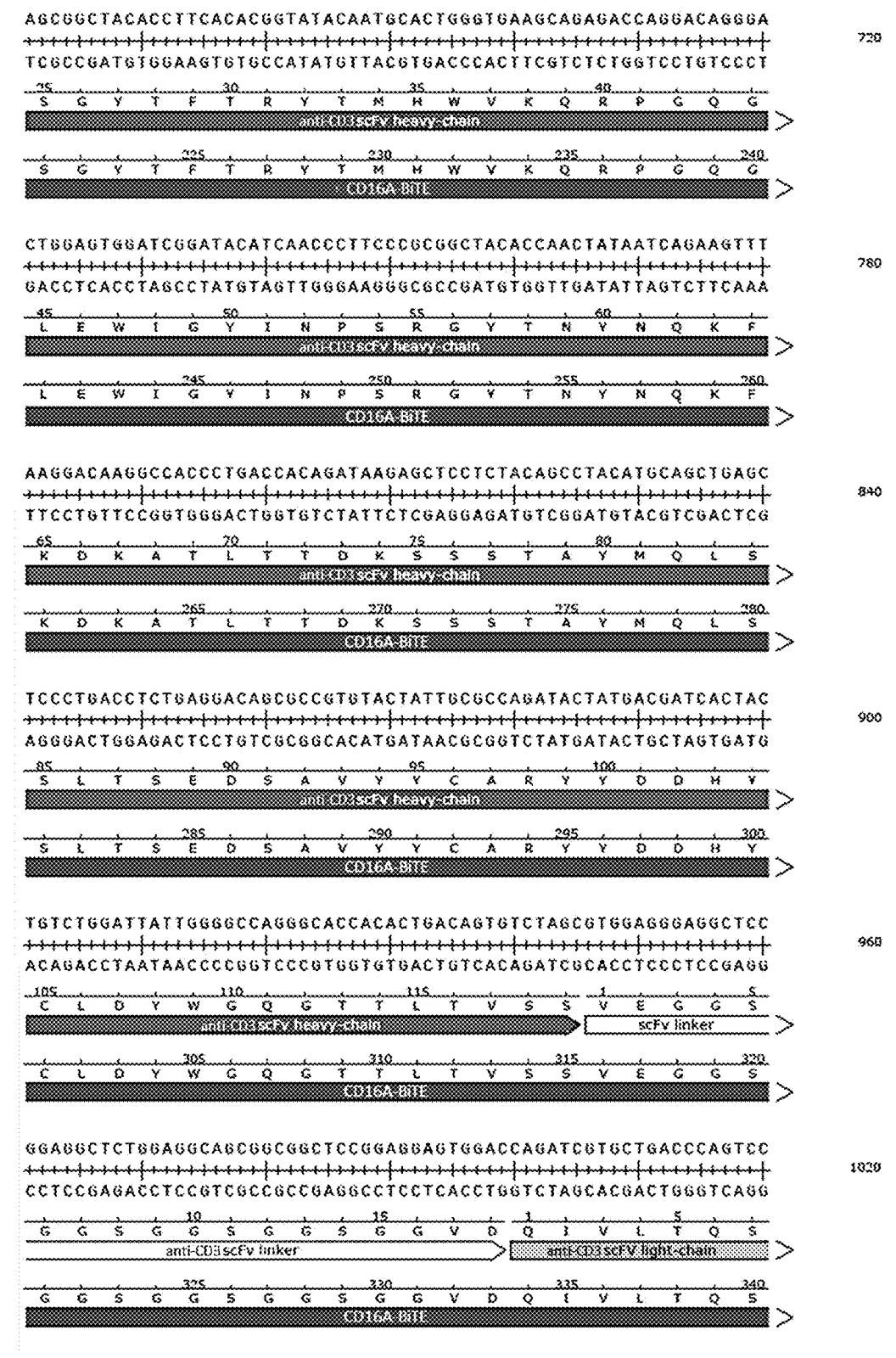
Figure 1G:
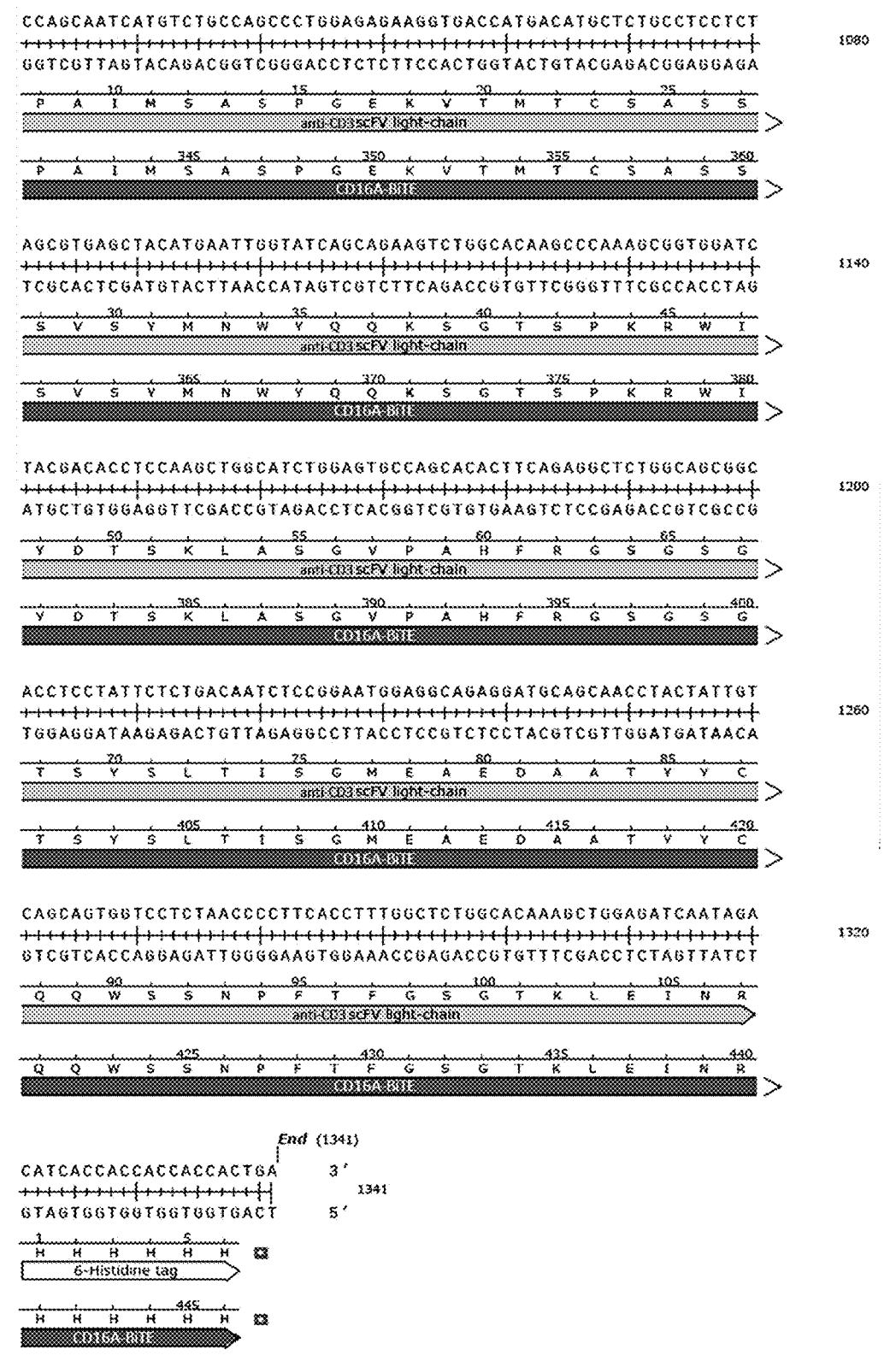

FIGS. 1A to 1G show genetic construction of the haCD16A-BiTE. FIG. 1A: The genetic construct of the haCD16A-CD3 bispecific T cell engager cloned in an adeno-associated virus (AAV) shuttle plasmid. H: 6×Histidine tag; ITR: inverted terminal repeat sequence of AAV; S: secretion signal; WPRE: woodchuck hepatitis B virus post-transcriptional regulatory element. FIG. 1B: The coding sequences of the extracellular domain (edCD16) of human high-affinity CD16A (haCD16A) and a single-chain antibody against human CD3 (anti-CD3 scFv) were fused in the same coding frame by gene synthesis. FIG. 1C: The synthesized gene with 1341 bp nucleotides encodes a fusion protein with 446 amino acids. FIGS. 1D to 1G: Scheme of the haCD16A-BiTE.

FIG. 2A: Analytical strategy of the haCD16A-BiTE binding to IgG antibody-coated cells. FIG. 2B: Antigen expression on tumor cells. FIG. 2C: The binding of the haCD16A-BiTE to IgG antibody-coated tumor cells. FIG. 2D: Analytical strategy of the haCD16A-BiTE binding to T cells. FIG. 2E: The binding of the haCD16A-BiTE to T cells.

DETAILED DESCRIPTION OF THE INVENTION

Figure 2A:
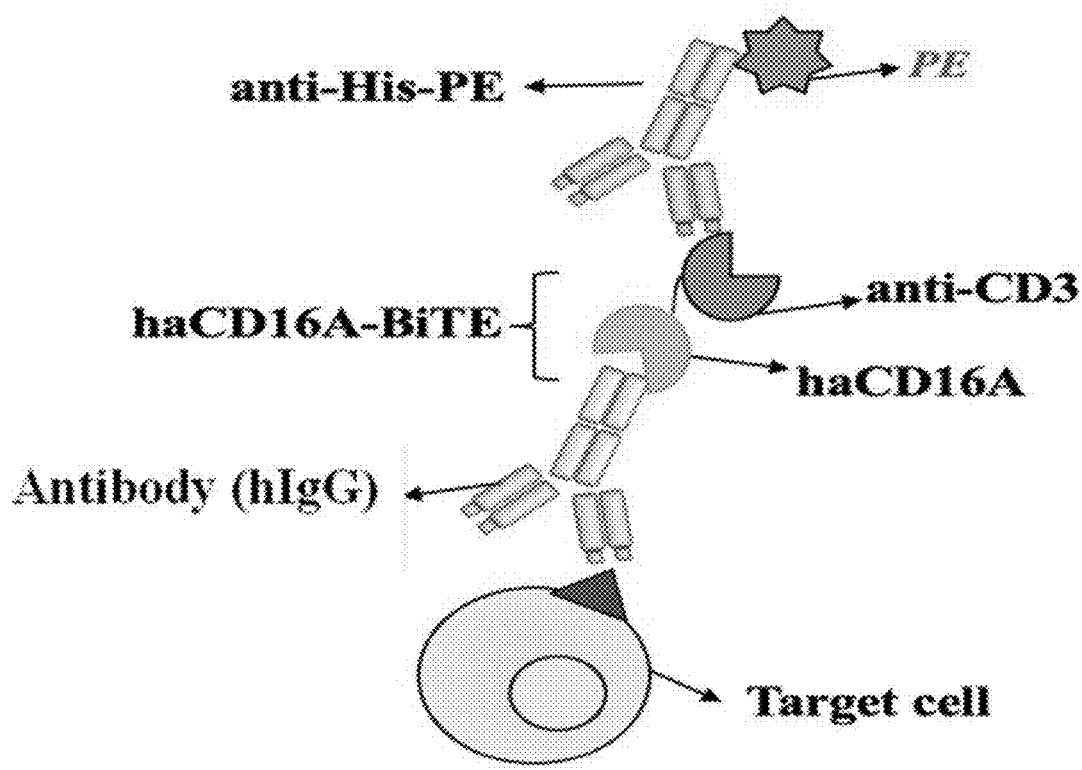
FIGS. 2A to 2E show the binding of the haCD16A-BiTEs to T cells and immunoglobulin G (IgG) antibody-coated tumor cells.

The present disclosure provides a fusion protein comprising:
- an Fc gamma receptor or ligand-binding fragment thereof; and
- an antibody or antigen-binding fragment thereof that specifically binds to an epitope on a surface antigen of T cells or a fragment thereof, wherein the surface antigen is able to trigger antibody-dependent cell-mediated cytotoxicity and/or to activate the T cells.

Particularly, the fusion protein according to the instant disclosure is known as a bispecific T cell engager that is provided with bispecific affinity to two antigens/ligands, acting as a bridge between a target cell and a T cell.

Preferably, the fusion protein activates ADCC immune response through which T cells can recognize and kill antibody-coated target cells expressing tumor- or pathogen-derived antigens on their surface.

Without combination with other treatment modalities, such as chemotherapy, monotherapies using direct-targeting of therapeutic mAbs to treat cancer generally result in limited therapeutic effects (Hiddemann et al., Blood, 106, 3725-32 (2005); Sehn et al., J Clin Oncol, 33, 3467-3474 (2015)). While not wishing to be limited by theory, the instant invention as disclosed herein is based on Applicant's idea that amplifying ADCC is a promising approach to increase the clinical benefits of therapeutic antibodies. The main immune effector cells mediating ADCC are natural killer (NK) cells (Wang et al., Front Immunol, 6, 368 (2015)). NK cells express Fc gamma receptors (FcγRs), mostly CD16A (FcγRIIIA), which recognize and bind to the Fc portion of IgG antibodies. Once the Fcγ receptor binds to the Fc region of IgG bound to the surface of target cells, the natural killer cell releases cytotoxic factors that cause the death of the target cell (Wang et al., Front Immunol, 6, 368 (2015)). Hence, ADCC involves three components: immune effector cells, antibodies, and target cells opsonized by the antibody. ADCC is triggered upon binding of FcγR expressed on the surface of NK cells to the Fc region of IgG molecules. It follows that affinity/quantities of FcγR and quality/quantities of NK cells could contribute to the differences in the magnitude of ADCC, given that genetic variation in FcγR resulting in different binding affinity is known to contribute to the differences in the magnitude of ADCC.

Examples of the Fc gamma receptors include but are not limited to CD16A, CD16B, CD32A, CD32B, CD64A, CD64B, and CD64C.

Examples of the antibody or antigen-binding fragment thereof that specifically binds to an epitope on a surface antigen of T cells or a fragment thereof include but are not limited to an anti-CD3 antibody, anti-4-1BB antibody, anti-CD28 antibody, or anti-OX40 antibody.

Preferably, the present disclosure provides a fusion protein comprising:
- an extracellular domain of human CD16A; and
- an antibody or antigen-binding fragment thereof that specifically binds to an epitope on human CD3 or a fragment thereof.

According to the disclosure, the fusion protein comprises an extracellular domain of CD16A. Preferably, the CD16A is human CD16A. CD16A, also known as FcγRIIIA, it is a transmembrane glycoprotein and there are two allelic variants of CD16A that have either a phenylalanine (F) or valine (V) residue at position 158. The CD16A-158V variant has a higher affinity for IgG, but CD16A-158F is the dominant allele in human population. Clinical analyses have revealed a positive correlation between the therapeutic efficacy of tumor-targeting therapeutic mAbs and CD16A binding affinity. Patients homozygous for the CD16A valine variant (CD16A-VN) had an improved clinical outcome after treatment with anti-tumor therapeutic antibodies compared to those who were either heterozygous (CD16A-V/F) or homozygous (CD16A-F/F) for the lower affinity CD16A isoform in response to clinically approved therapeutic antibodies such as rituximab, trastuzumab, and cetuximab (Cartron et al., Blood, 99, 754-758 (2002), Kim et al., Blood, 108, 2720-2725 (2006); Zhang et al., J Clin Oncol, 25, 3712-3718 (2007); Musolino et al., J Clin Oncol, 26, 1789-1796 (2008); Veeramani et al., Blood, 118, 3347-3349 (2011); Mellor et al., J Hematol Oncol, 6, 1 (2013)). However, only 10-20% of general population have high-affinity CD16A variant. In one preferred embodiment of the disclosure, the CD16A is a high-affinity CD16A variant.

In one more preferred embodiment of the disclosure, the extracellular domain of CD16A has an amino acid sequence of SEQ ID NO: 2 or a substantially similar sequence thereof.

As applied to polypeptides, the term "substantial similarity" or "substantially similar" means that a protein sequences, when optimally aligned with another (reference) protein sequence, such as by the programs GAP or BESTFIT using default gap weights, there is sequence identity in at least 90%, at least 95%, even more preferably at least 96%, 97%, 98% or 99% of amino acid residues, to the entire sequence of said reference protein sequence. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the an. Examples of groups of amino acids that have side chains with similar chemical properties include (1) aliphatic side chains: glycine, alanine, valine, leucine and isoleucine, (2) aliphatic-hydroxyl side chains: serine and threonine; (3)

amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters determine sequence homology or sequence identity between closely related polypeptides, such as homologous polypeptides from different species of organisms or between a wild type protein and a mutant thereof. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the disclosure to a database containing a is large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

According to the disclosure, the fusion protein comprises an antibody or antigen-binding fragment thereof that specifically binds to an epitope on human CD3 or a fragment thereof.

In immune response, CD3 is a surface antigen associated with the T-cell receptor (TCR) to form a complex involved in antigen recognition and signal transduction. The CD3 T cell co-receptor helps to activate both the cytotoxic T cell (CD8$^+$ T cells) and also T helper cells (CD4$^+$ T cells). Utilizing the fusion protein according to the disclosure, all of the CD3-expressing cells, including alpha-beta T cells, gamma-delta T cells, and natural killer T cells in the body could potentially be recruited, through the anti-CD3 portion of the fusion protein binding to the CD3 molecules on T cells, to become cells carrying high-affinity CD16A and capable of carrying out ADCC.

Various techniques known to persons of ordinary skill in the art can be used to determine whether an antibody "specifically binds to one or more amino acids" within a polypeptide or protein. Exemplary techniques include, e.g., routine cross-blocking assay such as that described in Antibodies, by Harlow and Lane (Cold Spring Harbor Press, Cold Spring Harb., N.Y.), alanine scanning mutational analysis, peptide blots analysis (Reineke, 2004, Methods Mol Biol 248:443-463), and peptide cleavage analysis. In addition, methods such as epitope excision, epitope extraction and chemical modification of antigens can also be employed (Tomer, 2000, Protein Science 9:487-496).

Another method that can be used to identify the amino acids within a polypeptide with which an antibody specifically binds is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues (bound by and) protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) Analytical Biochemistry 267(2):252-259; Engen and Smith (2001) Anal. Chem. 73:256A-265A.

The antibody according to the disclosure can be full-length or may comprise only an antigen-binding portion, and may be modified to affect functionality as needed.

The term "antibody", as used herein, means any antigen-binding molecule or molecular complex comprising at least one complementarity determining region (CDR) that specifically binds to or interacts with a particular antigen (e.g., CD3). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_{H1}$, $C_{H2}$ and $C_{H3}$. Each light chain comprises a light chain variable region (abbreviated herein as LCVR or $V_L$) and a light chain constant region. The light chain constant region comprises one domain ($C_{L1}$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the disclosure, the FRs of the anti-CD3 antibody (or antigen-binding portion thereof) may be identical to the human germline sequences, or may be naturally or artificially modified. An amino acid consensus sequence may be defined based on a side-by-side analysis of two or more CDRs.

The term "antibody", as used herein, also includes an antigen-binding fragment of a full antibody molecule. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. An antigen-binding fragment of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of an antigen-binding fragment of an antibody includes: (i) Fab fragments, (ii) F(ab')$_2$ fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody typically comprises at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) $V_H$-$C_{H1}$; (ii) $V_H$-$C_{H2}$; (iii) $V_H$-$C_{H3}$; (iv) $V_H$-$C_{H1}$-$C_{H2}$; (v) $V_H$-$C_{H1}$-$C_{H2}$-$C_{H3}$; (vi) $V_H$-$C_{H2}$-$C_{H3}$; (vii) $V_H$-$C_L$; (viii) $V_L$-$C_{H1}$; (ix) $V_L$-$C_{H2}$; (x) $V_L$-$C_{H3}$; (xi) $V_L$-$C_{H1}$-$C_{H2}$; (xii) $V_L$-$C_{H1}$-$C_{H2}$-$C_{H3}$; (xiii) $V_L$-$C_{H2}$-$C_{H3}$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present disclosure may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

In one preferred embodiment of the invention, the antibody or antigen-binding fragment thereof is an anti-CD3 single-chain variable fragment (scFv).

In another preferred embodiment of the invention, the antibody or antigen-binding fragment thereof has an amino acid sequence of SEQ ID NO: 4 or a substantially similar sequence thereof; preferably having at least 90%, at least 95%, at least 98% or at least 99% sequence identity or a substantially similar sequence thereof.

The antibody disclosed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present disclosure includes an antibody, and an antigen-binding fragment thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another mammalian germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present disclosure may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present disclosure.

The present disclosure also includes an anti-CD3 antibody comprising variants of any of the $V_H$, $V_L$, and/or CDR amino acid sequences disclosed herein having one or more conservative substitutions. For example, the present disclosure includes an anti-CD3 antibody having $V_H$, $V_L$, and/or CDR amino acid sequences with, e.g., 10 or fewer, 8 or fewer, 6 or fewer, 4 or fewer, etc. conservative amino acid substitutions relative to any of the $V_H$, $V_L$, and/or CDR amino acid sequences disclosed herein.

In one preferred embodiment of the disclosure, the extracellular domain of CD16 directly links to the antibody or antigen-binding fragment thereof. In another embodiment of the disclosure, a linker exists between the extracellular domain of CD16 and the antibody or antigen-binding fragment thereof.

In one preferred embodiment of the disclosure, the fusion protein further comprises a secretion signal peptide. The signal peptide (sometimes referred to as signal sequence, targeting signal, localization signal, localization sequence, transit peptide, leader sequence or leader peptide) as used herein refers to a short peptide located at the N-terminus of a protein that is destined towards the secretory pathway. In one embodiment of the disclosure, the secretion signal peptide has an amino acid sequence of SEQ ID NO: 6 or a substantially similar sequence thereof.

In one preferred embodiment of the disclosure, the fusion protein further comprises a protein purification tag.

In one preferred embodiment of the disclosure, the fusion protein has an amino acid sequence of SEQ ID NO: 8 or a substantially similar sequence thereof.

In another preferred embodiment of the disclosure, a novel bispecific T cell engager composed of the extracellular domain of the high-affinity CD16A variant and a single-chain anti-CD3 antibody (haCD16A-BiTE; FIG. 1A) effects the ADCC of mAbs in various fields of application. Such use of the haCD16A-BiTE provides several advantages: (1) overcoming limited availability of CD16A-expressing natural killer cells in the body, since with the haCD16A-BiTE, all of the CD3-expressing cells, including alpha-beta T cells, gamma-delta T cells, and natural killer T cells in the body could potentially be recruited, through the anti-CD3 portion of the haCD16A-BiTE binding to the CD3 molecules on T cells, to become cells carrying high-affinity CD16A and capable of carrying out ADCC; (2) resolving the issue of only 10-20% of general population expressing high-affinity CD16A variant which contributes to treatment efficacy of approved mAbs by applying the haCD16A-BiTE to any individual and consequently endowing large number of $CD3^+$ T cells in each individual with high-affinity CD16A through the binding of the anti-CD3 portion of the haCD16A-BiTE to the CD3 molecules on T cells; (3) circumventing the down-regulation of CD16A on activated NK cells through adopting the extracellular domain of high-affinity CD16A in the design of this haCD16A-BiTE; (4) creating the feasibility of ADCC-mediated depletion of unwanted cells in T cell expansion culture prepared for immunotherapy by endowing T cells with ADCC activity with this haCD16A-BiTE; (5) providing a potential approach to create a viral vaccine with antibody-induced ADCC capability through the combined use of a vaccine and this haCD16A-BiTE and to increase treatment efficacy of antibody therapy of virally-infected diseases; (6) transforming suppression-removed T cells in patients receiving immune checkpoint inhibitor into T cells with ADCC activity to increase the therapeutic potential of avelumab-like anti-PD-L1 mAbs.

The present disclosure also provides a polynucleotide encoding the fusion protein as disclosed herein.

Preferably, the polynucleotide comprises a fragment encoding the extracellular domain of high-affinity CD16A and has a nucleic acid sequence of SEQ ID NO: 1 or a substantially identical sequence thereof.

Preferably, the polynucleotide comprises a fragment encoding the antibody or antigen-binding fragment thereof and has a nucleic acid sequence of SEQ ID NO: 3 or a substantially identical sequence thereof.

Preferably, the polynucleotide further comprises a fragment encoding a secretion signal peptide and has a nucleic acid sequence of SEQ ID NO: 5 or a substantially identical sequence thereof.

Preferably, the polynucleotide further comprises a fragment encoding a protein purification tag.

More preferably, the polynucleotide has a nucleic acid sequence of SEQ ID NO: 7 or a substantially identical sequence thereof.

The term "substantial identity" or "substantially identical," when referring to a nucleic acid or a fragment thereof, indicates that, when optimally aligned with appropriate nucleotide insertions or deletions with another (reference) nucleic acid (or its complementary strand), there is nucleotide sequence identity in at least 95%, and more preferably at least 96%, 97%, 98% or 99%, of the nucleotide bases, to the entire sequence of said reference nucleic acid sequence as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

In one preferred embodiment of the disclosure, the fusion protein can be produced using any number of expression systems, including prokaryotic and eukaryotic expression systems. Many such systems are widely available from commercial suppliers. In one embodiment, the fusion protein may be expressed using a vector, wherein the polynucleotide encoding said fusion protein is operably linked to a promoter sequence. In one embodiment, the promoter is a constitutive promoter. In another embodiment, the promoter is an inducible promoter.

In one embodiment, the polynucleotide or vector is contained in a virus. In another embodiment, the virus is selected from the group consisting of a retrovirus, a lentivirus, an adenovirus, and an adeno-associated virus. In one preferred embodiment of the disclosure, the polynucleotide or vector is contained in an adeno-associated virus shuttle plasmid.

The present disclosure also provides a host cell comprising the polynucleotide as disclosed herein. In one embodiment, the host cell is a prokaryotic cell. In another embodiment, the host cell is an eukaryotic cell. In another embodiment, the host cell is a mammalian cell. In a preferred embodiment, the host cell is a human cell.

Preferably, the host cell comprises an adeno-associated virus vector which comprises the polynucleotide as disclosed herein.

The present disclosure also provides a pharmaceutical composition comprising a therapeutically effective amount of the fusion protein as disclosed herein and optionally a pharmaceutically acceptable carrier or excipient.

The present disclosure also provides a pharmaceutical composition comprising a therapeutically effective amount of the host cell according to the disclosure. A bispecific T cell engager generally has a very short serum half-life, around 2 hours. This results in the application of BITE® requiring continuous intravenous infusion, which procedure is inconvenient for human use. A virus is preferably used to mediate in vivo continuous production of BITE® to overcome this shortcoming.

The pharmaceutical compositions of the disclosure are formulated with suitable carriers, excipients, and other agents that provide improved transfer, delivery, tolerance, and the like A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™, Life Technologies, Carlsbad, Calif), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of fusion protein administered to a patient may vary depending upon various factors, including the age and the size of the patient, target disease, conditions, route of administration, and the like. The preferred dose is typically calculated according to body weight or body surface area. Depending on the severity of the condition, the frequency and the duration of the treatment can be adjusted. Effective dosages and schedules for administering the fusion protein may be determined empirically; for example, patient progress can be monitored by periodic assessment, and the dose adjusted accordingly. Moreover, interspecies scaling of dosages can be performed using well-known methods in the art (e.g., Mordenti et al., 1991, Pharmaceut. Res. 8.1351).

Various delivery systems are known and can be used to administer the pharmaceutical composition of the disclosure, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Routes of administration include, but are not limited to, intradermal, intramuscular, intraperitoneal, intravenous, intratumorous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In one embodiment of the invention, a pharmaceutical composition of the present disclosure can be delivered intratumorous, subcutaneously or intravenously with a standard needle and syringe.

In certain situations, the pharmaceutical composition can be delivered in a controlled release system. In one embodiment, a pump may be used (see Langer, supra; Sefton, 1987, CRC Crit Ref. Biomed. Eng. 14:201) In another embodiment, polymeric materials can be used; see, Medical Applications of Controlled Release. Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

In certain situations, the pharmaceutical composition can be delivered in an injectable preparation. The injectable preparations may include dosage forms for intratumorous, intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the pharmaceutical composition in a sterile aqueous medium or an oily medium conventionally used for injections Examples of the aqueous medium for injections include physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. Examples of the oily medium include sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

The present disclosure also provides use of the pharmaceutical composition as disclosed herein in the manufacture of a medicament for inducing antibody-dependent cellular cytotoxicity in a subject in need.

Preferably, the present disclosure provides use of the pharmaceutical composition in the manufacture of a medicament for the treatment of a cancer, infectious disease, autoimmune disease, graft versus host disease, or post-transplantation lymphoproliferative disease in a subject in need.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. The terms "preventing" and "prevention" refer to the administration of an agent or composition to a clinically asymptomatic individual who is susceptible to a particular adverse condition, disorder, or disease, and thus relates to the prevention of the occurrence of symptoms and/or their underlying cause. As is understood by one skilled in the art, prevention or preventing need not achieve absolute (complete) block or avoidance of the conditions. Rather, prevention may achieve substantial (e.g., over about 50%) reduction or avoidance of the diseases or conditions to be prevented. Unless otherwise indicated herein, either explicitly or by implication, if the term "treatment" (or "treating") is used without reference to possible prevention, it is intended that prevention be encompassed as well.

"Cancer", "tumor", "transformed" and like terms include precancerous, neoplastic, transformed, and cancerous cells, and can refer to a solid tumor, or a non-solid cancer (see, e.g., Edge et al. AJCC Cancer Staging Manual (7th ed. 2009); Cibas and Ducatman Cytology: Diagnostic principles and clinical correlates (3rd ed. 2009)). Cancer includes both benign and malignant neoplasms (abnormal growth). "Transformation" refers to spontaneous or induced phenotypic changes, e.g., immortalization of cells, morphological changes, aberrant cell growth, reduced contact inhibition and anchorage, and/or malignancy (see, Freshney, Culture of Animal Cells a Manual of Basic Technique (3rd ed. 1994)). Although transformation can arise from infection with a transforming virus and incorporation of new genomic DNA, or uptake of exogenous DNA, it can also arise spontaneously or following exposure to a carcinogen.

In one preferred embodiment of the disclosure, the pharmaceutical composition further comprises an antibody or antibodies. More preferably, the antibody is an IgG antibody. In another aspect, the antibody is a monoclonal antibody or polyclonal antibody. Examples of the antibody include but are not limited to an anti-CD20 antibody, anti-EGFR antibody, anti-HER2 antibody, anti-latent membrane protein 1 (LMP1) antibody, or anti-PD-L1 antibody.

Cancer development and progression are characterized by evasion of immune responses, including tumor escape mediated through immune checkpoint pathways (Pardoll Nat Rev Cancer, 12, 252-264 (2012)). By overexpressing PD-L1, tumor cells exploit the PD-1/PD-L1 pathway to promote an immunosuppressive environment and allow tumor growth (Topalian et al., Curr Opin Immunol, 24, 207-212 (2012)). Blocking PD-L1 inhibitory signals can restore T-cell anti-tumor activity and thus represents a key therapeutic strategy (Topalian et al., Curr Opin Immunol, 24, 207-212 (2012); Postow et al., J Clin Oncol, 33, 1974-1982 (2015)). Avelumab, an approved human IgG anti-PD-L1 mAb, is thought to specifically bind to PD-L1, preventing the interaction between PD-L1 and the inhibitory T-cell receptor PD-1. PD-L1 blockade removes the suppression of T-cell activity, resulting in T-cell-mediated anti-tumor immune responses (Hamilton and Rath Expert Opinion on Biological Therapy, 17, 515-523 (2017)). In addition, unlike other approved anti-PD-L1 antibodies, avelumab has a wild-type IgG Fc region, which enables avelumab to engage with FcγRs on NK cells and induce tumor-directed ADCC (Boyerinas et al., Cancer Immunol Res, 3, 1148-1157 (2015); Hamilton and Rath Expert Opinion on Biological Therapy, 17, 515-523 (2017)). Consequently, avelumab has the potential to both reactivate T cell-mediated antitumor immune responses and mediate eradication of tumor cells by ADCC. The pharmaceutical composition according to the disclosure endows these suppression-removed T cells with ADCC activity and significantly increases the numbers of cell with ADCC activity and therapeutic potential of mAbs.

In one embodiment of the disclosure, the fusion protein is applied to delete unwanted cells. For example, to mitigate graft versus host disease and to prevent post-transplantation lymphoproliferative disease, such as post-transplantation Epstein-Barr virus (EBV)-induced lymphoproliferative disease.

In one embodiment of the disclosure, the fusion protein is applied to treat infectious diseases. According to the present disclosure, the infectious disease preferably includes viral infection, such as human immunodeficiency virus (HIV), Hepatitis B Virus (HBV), Epstein-Barr virus (EBV), and Cytomegalovirus (CMV). Not to be limited by theory, it is believed that ADCC is a potentially important protection mechanism in HIV vaccine (Haynes et al., N Engl J Med, 366, 1275-1286 (2012); Parsons et al., Retrovirology, 15, 58 (2018)). In addition, eliminating latently infected cells, which harbor the viral reservoir, is a major effort in HIV treatment. Many highly potent neutralizing antibodies that neutralize broad arrays of HIV-1 isolates, termed broadly neutralizing antibodies, have been isolated in recent years (Mujib et al., J Virol, 91, e00634-17 (2017)). Passive transfer of the broadly neutralizing antibody-VRC01 is currently under clinical evaluation for its potential to eliminate latently infected cells (NCT02716675 and NCT02568215) and there is a body of evidence suggesting NK cell-mediated ADCC lies in its potential ability to eliminate latently infected cells (Madhavi et al., J Virol, 91, e00700-17 (2017)). Nonetheless, chronic HIV-1 infection has been demonstrated to alter the phenotype, functionality and subset distribution of NK cells. Novel approaches to enhance ADCC, such as that disclosed herein, in HIV-infected patients could critically contribute to achieve a cure for HIV. Similar strategies could also be applied to vaccine design and treatment of other viral infections, such as HBV, EBV, and CMV (Gao et al., Human Vaccines Immunotherapeutics, 13, 1768-1773 (2017); Coghill et al., Clin Cancer Res, 22, 3451-3457 (2016); McVoy et al., Int J Mol Sci, 19, 3982 (2018)).

The following examples are provided to aid those skilled in the art in practicing the present disclosure.

EXAMPLES

Example 1 haCD16A-BiTE Construct

The genetic construction of haCD16A-BiTE is shown in FIGS. 1A to 1G. FIG. 1A: The genetic construct of CD16A-CD3 bispecific T cell engager was cloned in an adeno-associated virus (AAV) shuttle plasmid pAAV-CD16CD3 and driven by the cytomegalovirus promoter (CMV) for the expression of a fusion protein with 446 amino acids. H: 6×Histidine tag; ITR: inverted terminal repeat sequence of AAV; S: secretion signal; WPRE: woodchuck hepatitis B virus post-transcriptional regulatory element. FIG. 1B: The coding sequences of the extracellular domain (edCD16) of human high-affinity CD16A and a single-chain antibody against human CD3 (anti-CD3 scFv) were fused in the same coding frame by gene synthesis. FIG. 1C: The synthesized gene with 1341 bp nucleotides encodes a fusion protein with 446 amino acids. FIGS. 1D to 1G: Scheme of haCD16A-BiTE.

In Vitro Binding Assay of the haCD16A-BiTE.

The haCD16A-BiTE has the ability to bind human IgG antibodies and T cells. This binding capability of the haCD16A-BiTE was first demonstrated. The haCD16A-BiTE with histidine-tags were produced and purified from supernatants of the haCD16A-BiTE gene-transfected HEK 293 cells by affinity chromatography. To demonstrate the binding of the haCD16A-BiTE to IgG antibodies, the analytical strategy is outlined in FIG. 2A. Raji (CD20$^+$ Burkett lymphoma cells) and A431 (EGFR$^+$ epidermoid carcinoma cells) cells were first incubated with 1·g of rituximab and cetuximab (both are IgG antibodies) respectively for 10 minutes and then with 50 ng of the haCD16A-BiTE in 100 μl of PBS at 4° C. for 10 minutes. Next, cells were pelleted by centrifugation at 400×g for 5 minutes, washed once with PBS, and incubated with 2 μl of a PE-labeled anti-6×-histidine tag antibody (Miltenyi Biotech) in 100 μl of PBS at 4° C. for 1 hour. After washing once with PBS, cells were subjected to flow cytometry analysis, and the data were expressed as a histogram with counts versus fluorescence. Raji and A431 cells were also examined for CD20 and EGFR expression by flow cytometry.

Figure 2B:
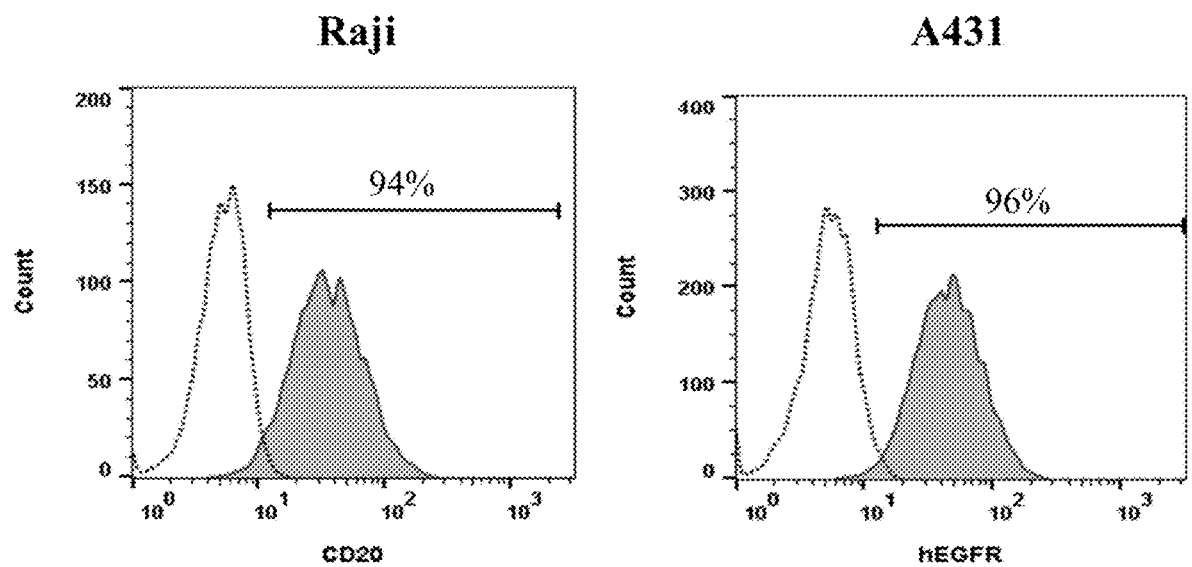
Figure 2C:
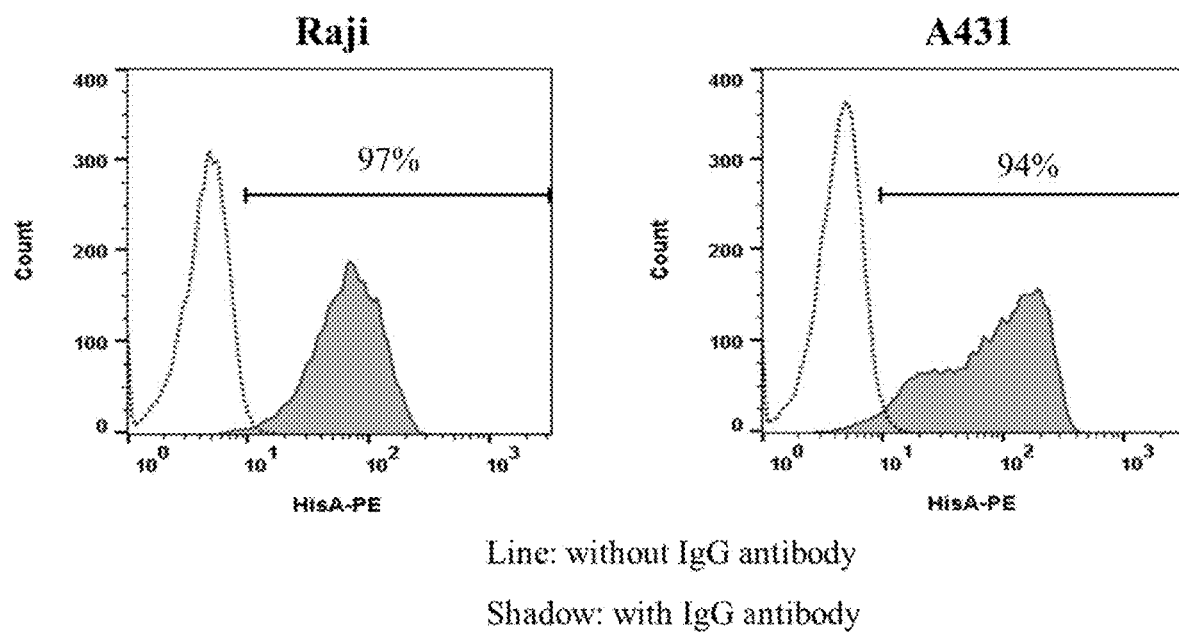

As shown in FIG. 2B, Raji and A431 cells expressed CD20 and EGFR, respectively. In the presence of the haCD16A-BiTEs, more than 90° % of Raji or A431 cells treated with rituximab or anti-EGFR antibodies were stained positive with the anti-6×-histidine tag (anti-His) antibody, but not untreated cells (FIG. 2C), indicating the haCD16A-BiTE has the ability to bind IgG antibody. These experimental data demonstrate the haCD16A-BiTEs are able to bind to IgG antibody-coated tumor cells.

Figure 2D:
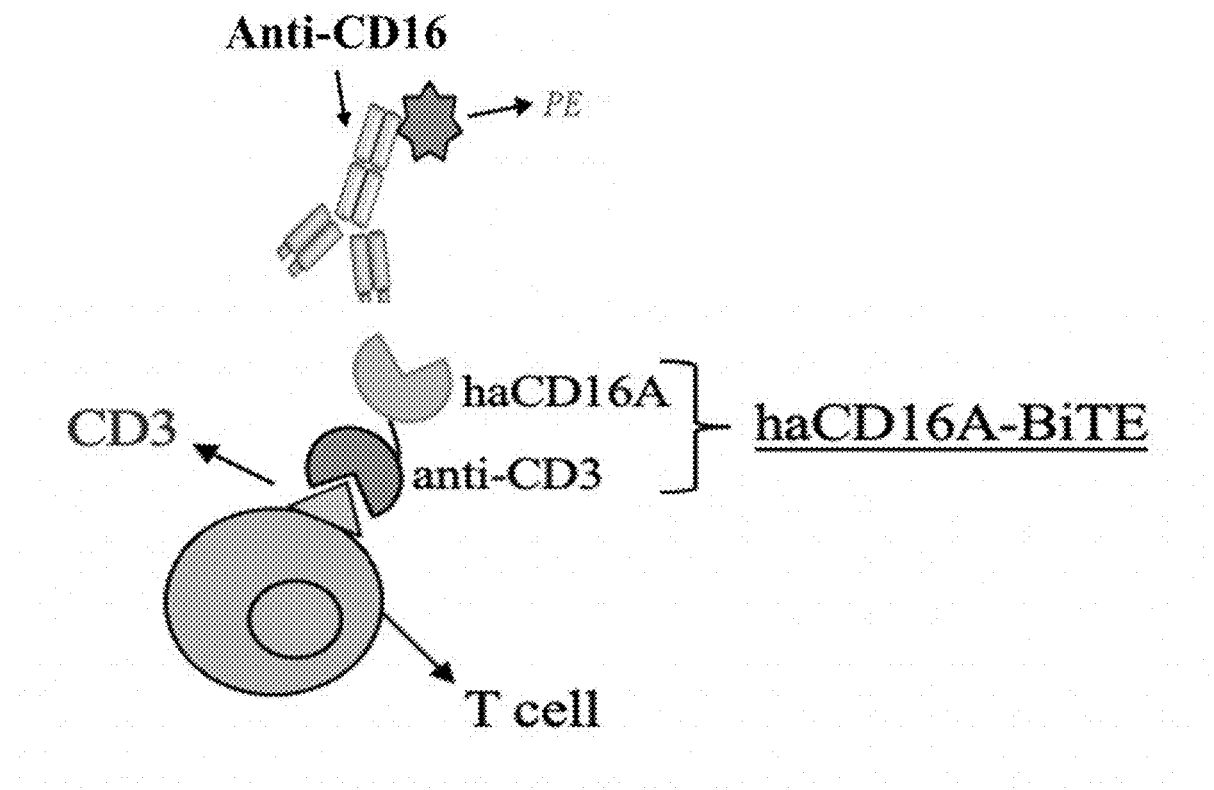
Figure 2E:
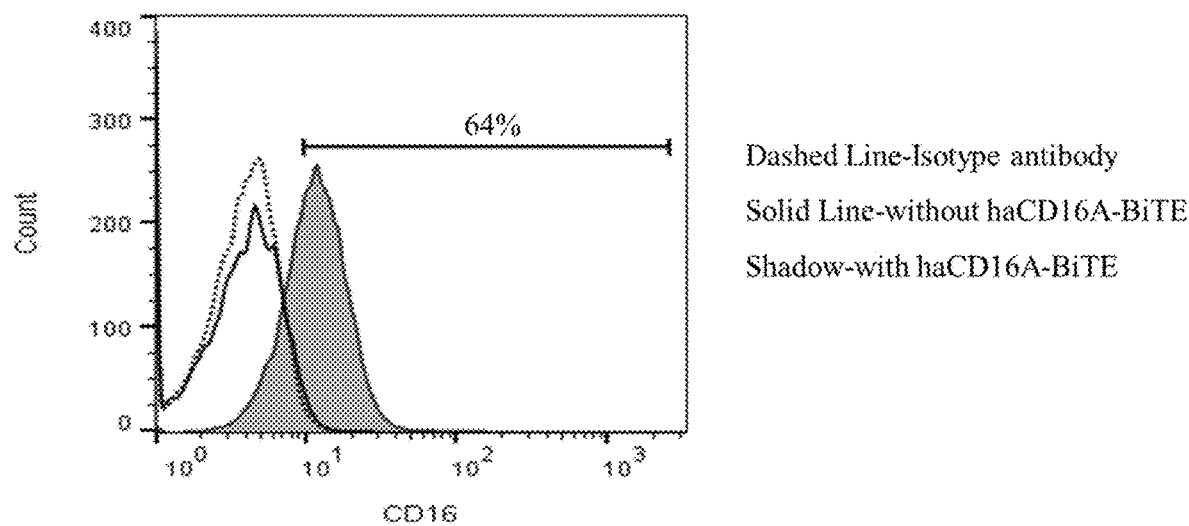

To show the binding of the haCD16A-BiTE to T cell, FIG. 2D illustrates the analytical strategy and FIG. 2E shows CD16-negative T cells, more than 95% of which expressing CD3 molecules, were detected by anti-CD16 antibody in the presence of the haCD16A-BiTEs, but not without the haCD16A-BiTEs. These results indicate the haCD16A-BiTE binds to T cells. The experimental methods used were as above described, except CD16$^+$ T cells were used and IgG antibodies were omitted.

Example 2

In Vitro Activity Assay of the haCD16A-BiTE.
Ability of the haCD16A-BiTE to Mediate CD20-Expressing Tumor Cell Killing in the Presence of Approved Anti-CD20 IgG Antibody (Rituximab) and T Cells.

The cytotoxicity experiment was carried out in accordance with the method disclosed in Sheehy et al. (J Immunol Methods, 249, 99-110 (2001)) In this experiment, CD20-expressing Raji, VAL, and Toeldo blood tumor cell lines were used as target cells, wherein the VAL cell line was acute lymphocytic leukemia (ALL) cells, and Toeldo cell line was diffuse large B cell lymphoma cells. The RS4 cell line was CD20⁻ ALL cells. Raji, VAL, Toeldo, and RS4 cells were independently stained with 5(6)-carboxyfluorescein diacetate succinimidyl ester (CFSE) and seeded in the wells of culturing plates ($5\times10^4$/well). The haCD16A-BiTEs (80 ng/well), rituximab (10 µg/well), and T cells ($5\times10^5$ cells/well) were added independently or together into each of the wells containing different tumor cells. After cultures were incubated for 6 hours, the viability of the cells was determined by counting CFSE cells using flow cytometry. T cells were obtained from peripheral blood mononuclear cells (PBMC) cultures expanded with CD3/CD28 beads, IL-7, and IL-15, according to methods described by Chen et al. (Clinical Immunology, 104, 58-66, (2002)).

Figure 3:
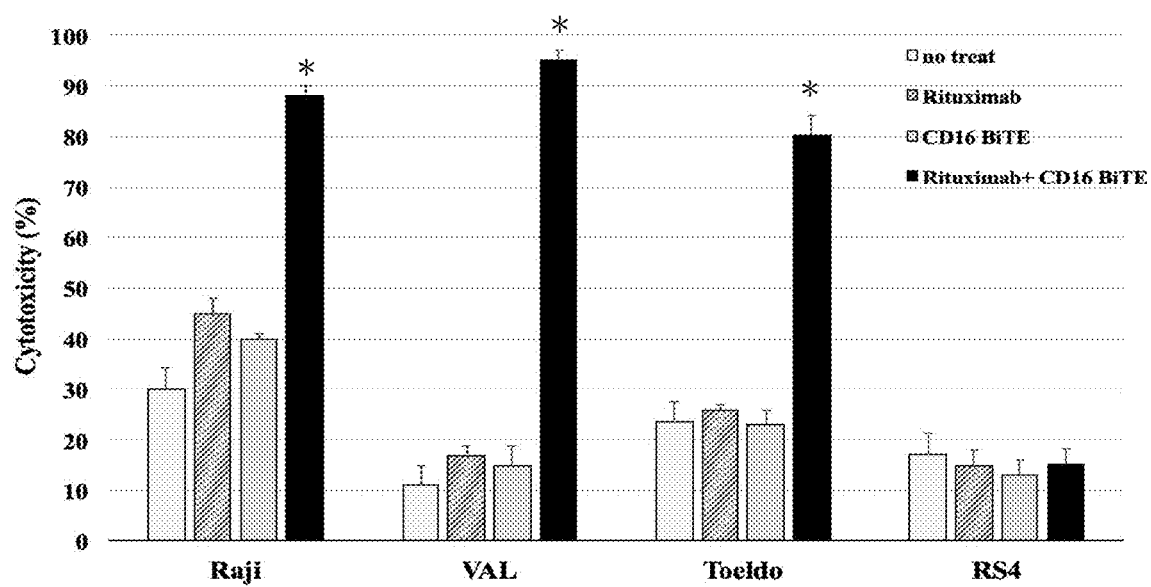
FIG. 3 shows the effect on killing of CD20-expressing cell lines by treatment of said cell lines with anti-CD20 antibodies (Rituximab, Rituxin®) and the haCD16A-BiTEs alone or in combination in the presence of T cells.

The results as shown in FIG. 3 prove that, in the presence of T cells, the haCD16A-BiTE exhibits a synergistic effect in killing CD20-expressing blood tumor cells (Raji, VAL and Toeldo) when combined with rituximab, as compared to using the haCD16A-BiTE or rituximab alone. *$p<0.001$, compared to the haCD16A-BiTE or rituximab alone.
Ability of the haCD16A-BiTE to Mediate EGFR-Expressing Tumor Cell Killing in the Presence of Approved Anti-EGFR IgG Antibodies (Cetuximab) and T Cells.

The experiment was carried out exactly as described in FIG. 3, except that EGFR-expressing tumor cell line (A431) and cetuximab (2.5 µg/well) were used instead. In this experiment, A431 cells expressing EGFR molecules were used as target cells. The MCF-7 cell line was EGFR-low breast tumor cells.

Figure 4:
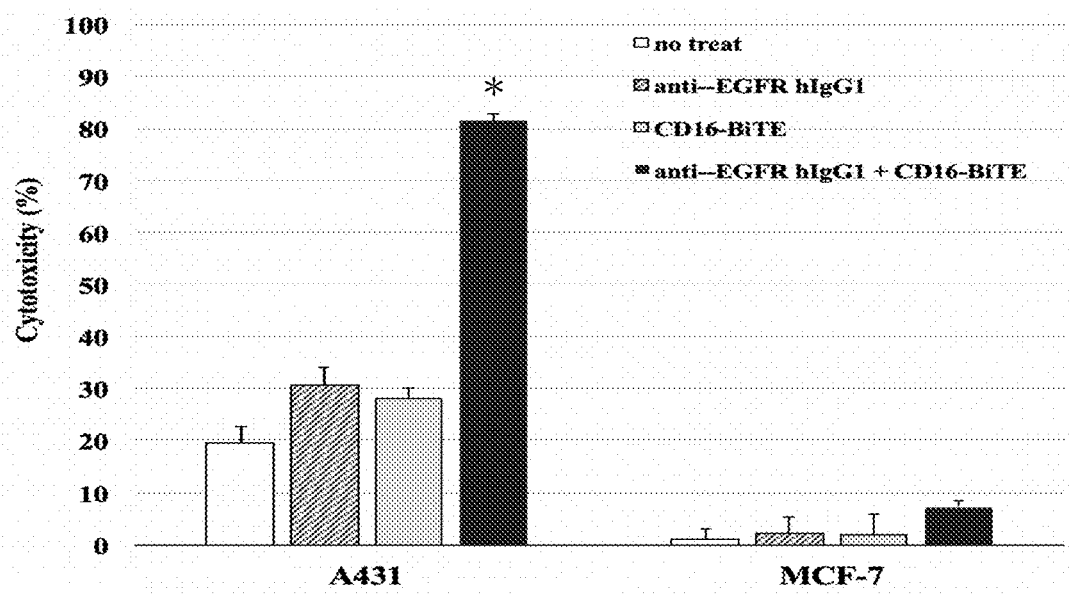
FIG. 4 shows the effect on killing of epidermal growth factor receptor (EGFR)-expressing cell line by treatment of said cell line with anti-EGFR antibodies (Cetuximab, Erbitux®) and the haCD16A-BiTEs alone or in combination in the presence of T cells.

The results as shown in FIG. 4 prove that in the presence of T cells, the haCD16A-BiTE exhibits a synergistic effect in killing EGFR-expressing cells (A431) when combined with cetuximab, as compared to using the haCD16A-BiTE or cetuximab alone. *$p<0.001$, compared to the haCD16A-BiTE or cetuximab alone.
Ability of the haCD16A-BiTE to Mediate HER2-Expressing Tumor Cell Killing in the Presence of Approved Anti-HER2 IgG Antibodies (Trastuzumab) and T Cells.

The experiment was carried out exactly as described in FIG. 3, except that HER2-expressing tumor cell line and trastuzumab (2.5 µg/well) were used instead. In this experiment, BT474 tumor cell line expressing HER2 molecules in >80% of cells were used as target cells, wherein BT474 was breast ductal carcinoma cell. The T47D cell line was HER2-low mammary gland ductal carcinoma cells with 10° % of cells expressing HER2 in low density.

Figure 5:
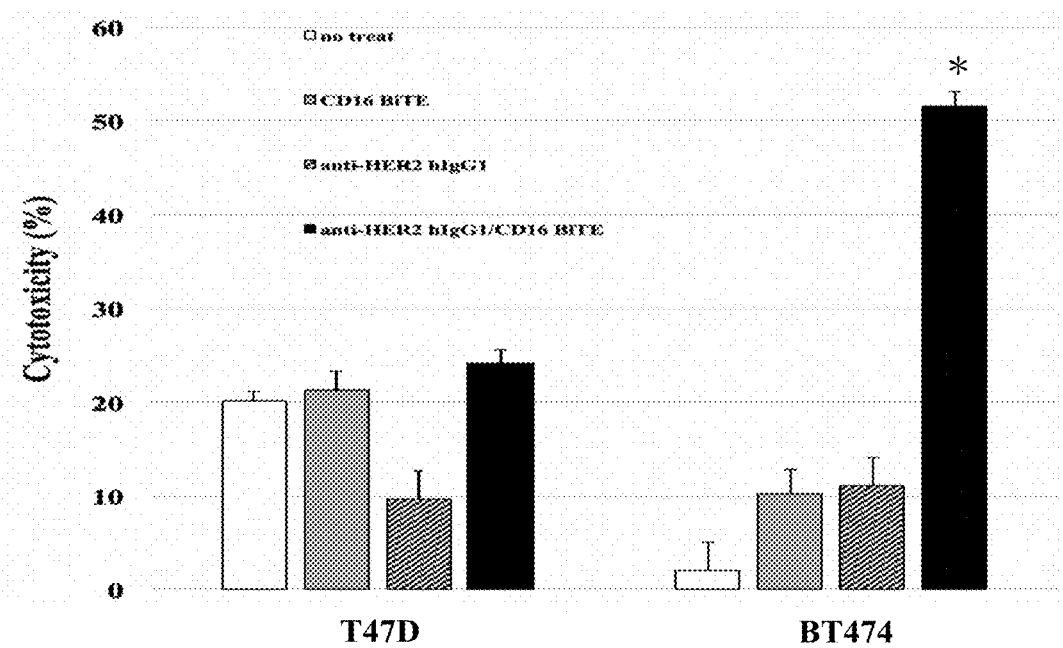
FIG. 5 shows the effect on killing of human epidermal growth factor receptor 2 (HER2)-expressing cell line by treatment of said cell line with anti-HER2 antibodies (Trastuzumab, Herceptin®) and the haCD16A-BiTEs alone or in combination in the presence of T cells.

The results as shown in FIG. 5 prove that in the presence of T cells, the haCD16A-BiTE exhibits a synergistic effect in killing HER2-high cells (BT474 cells), but not HER2-low cells (T47D cells) when combined with trastuzumab, as compared to using the haCD16A-BiTE or trastuzumab alone. *$p<0.01$, compared to the haCD16A-BiTE or trastuzumab alone.

Altogether, experimental data as shown in Example 2 demonstrate that the haCD16A-BiTE is able to recruit T cells to mediate killing of IgG antibody-bound tumor cells. Importantly, these results also demonstrate that haCD16A-BiTE is able to combined with various FDA-approved IgG therapeutic antibodies to kill tumor cells.

Example 3

The Effect of Blood Plasma on the Activity of the haCD16A-BITE

Normal plasma levels of IgG may compete with therapeutic mAbs of IgG isotype for binding to the haCD16A-BiTE resulting in loss of the haCD16A-BiTE activity. To evaluate this competition, whole blood from healthy individuals was centrifuged at 400×g for 5 minutes and the supernatants were taken as blood plasma. Plasma was added, at different volume ratios, to the serum-free medium used for cytotoxicity assay experiments illustrated in FIG. 3 to analyze the effect of plasma on the cytotoxicity of rituximab in the presence of the haCD16A-BiTE and T cells. Plasma also mediates complement-dependent cytotoxicity of rituximab, thus data were expressed by subtracting out that of the cytotoxicity of rituximab/plasma/T cells.

Figure 6:
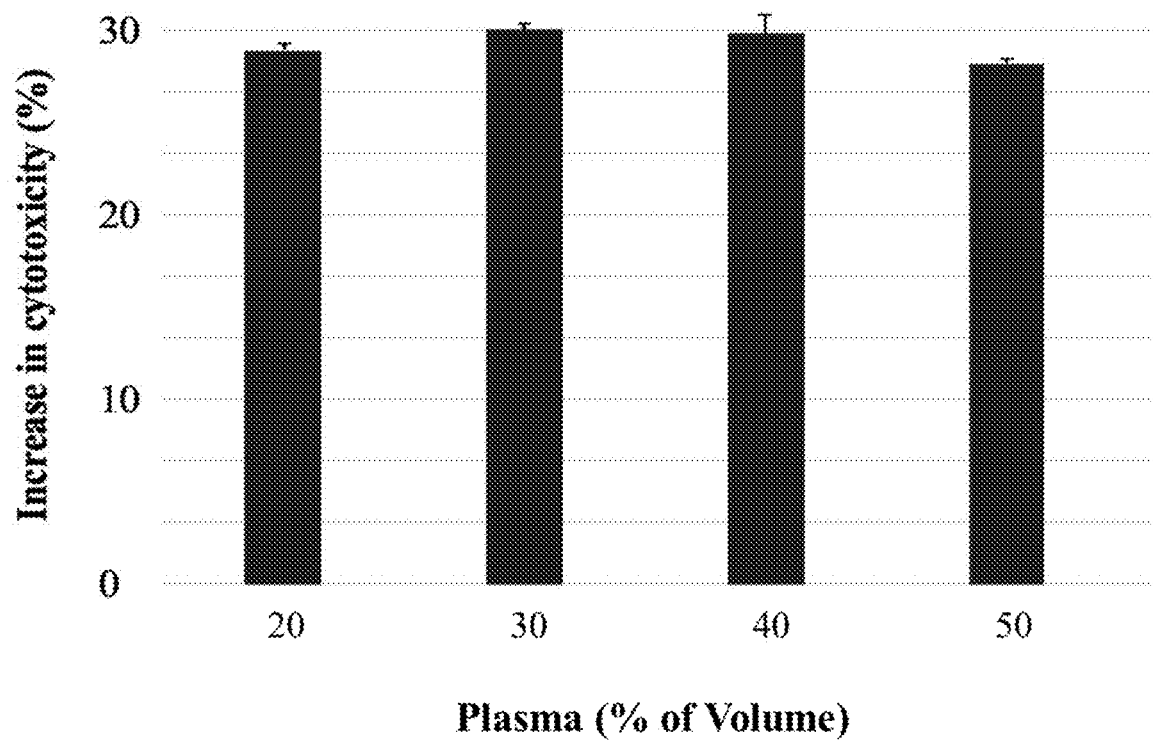
FIG. 6 shows the effect of plasma on killing of CD20-expressing cell line treated with Rituximab and the haCD16A-BiTEs.

FIG. 6 shows that blood plasma, up to 50%, did not significantly reduce the cytotoxicity of rituximab on Raji cells in the presence of the haCD16A-BiTE and T cells.

Example 4

Figure 7A:
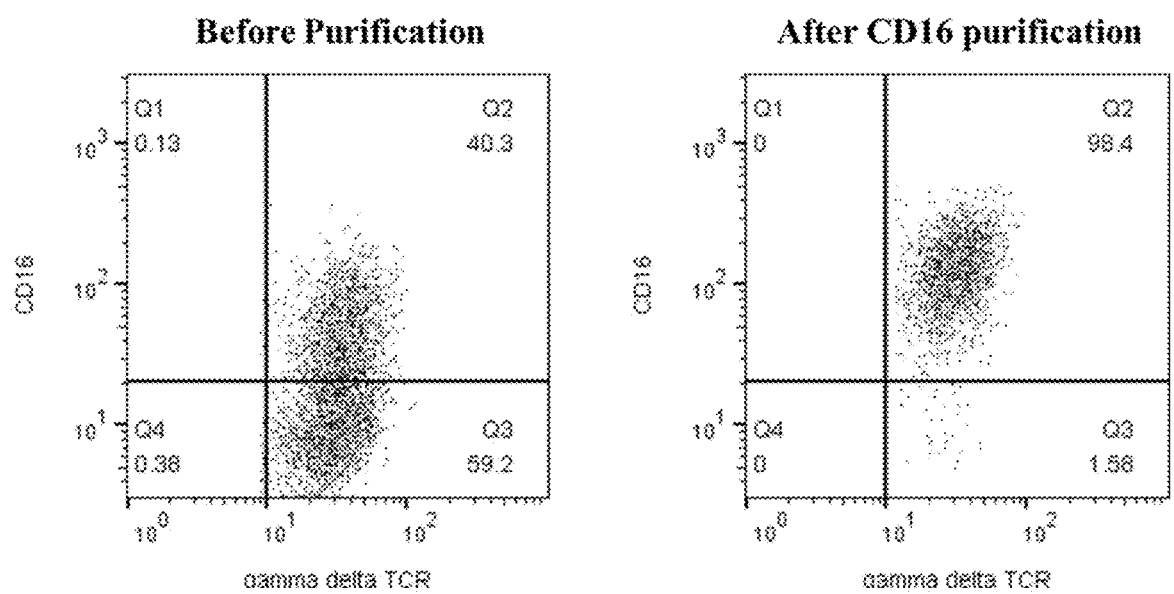
FIGS. 7A and 7B show comparison study of IgG antibody-mediated cell killing between CD16⁻ γ9δ2 T cells pulsed with the haCD16A-BiTEs and CD16⁺ γ9δ2 T cells.

Comparison Study of IgG Antibody-Mediated Cell Killing Between CD16⁺ γ9δ2 T Cells and CD16⁻γ 9δ2 T Cells Pulsed with the haCD16A-BiTEs To evaluate the equivalence of the haCD16A-BiTEs to the high-affinity CD16A expressed on T cells, we compared the antibody-mediated cytotoxicity of CD16⁺γ9Ω T cells pulsed with the haCD16A-BiTEs with that of CD16⁺γ9δ2 T cells having a high affinity CD16 variant.

γ9δ2 T cells were generated as described below. PBMC ($2\times10^6$ cells/ml) from different donors were stimulated with recombinant human IL2 (25 ng/ml; Prospec) and Zoledronate (1 µM, Sigma) for 14 days in RPMI-1640 medium containing 10% heat-inactivated FBS, penicillin (100 IU/ml), and streptomycin (100 µg/ml) at 37° C. in a humidified incubator with 5% $CO_2$. Subsequently, γ9δ2 T cell cultures were analyzed for CD16 expression and for those cultures stained positive for CD16, a polymerase chain reaction specific for CD16 high-affinity variant was performed to select high-affinity variant cultures of CD16⁺-γ9δ2 T cells. CD16⁺-γ9δ2 T cells were purified with an anti-PE purification kit from Miltenyi Biotech coupling with an anti-CD16 antibody labelled with PE according to the manufacturer's instruction and >95% of these purified 7982 T cells express CD16 (FIG. 7A). Those cultures stained negative for CD16 expression were used as cell sources of CD16⁻-γ9δ2 T cells.

Antibody-mediated cell killing were analyzed according to methods described in Example 2 using rituximab and Raji cell as target cell. To study antibody-mediated cell killing of CD16⁺-γ9δ2 T cells, Raji were stained with CFSE and seeded in the wells of culturing plates ($5\times10^4$/well) with rituximab (20 µg/well) and CD16⁺-γ9δ2 T cells ($5\times10^5$ cells/well). To evaluate antibody-mediated cell killing of CD16⁻-γ9δ2 T cells in combination with the haCD16A-BiTEs, Raji cells stained with CFSE ($5\times10^4$/well), haCD16A-BiTE (80 ng/well), Rituximab (20 µg/well), and CD16⁺-γ9δ2 T cells ($5\times10^5$ cells/well) were added together into the wells. After cultures being incubated for 6 hours, the viability of Raji cells was determined by counting CFSE*cells using flow cytometry.

Figure 7B:
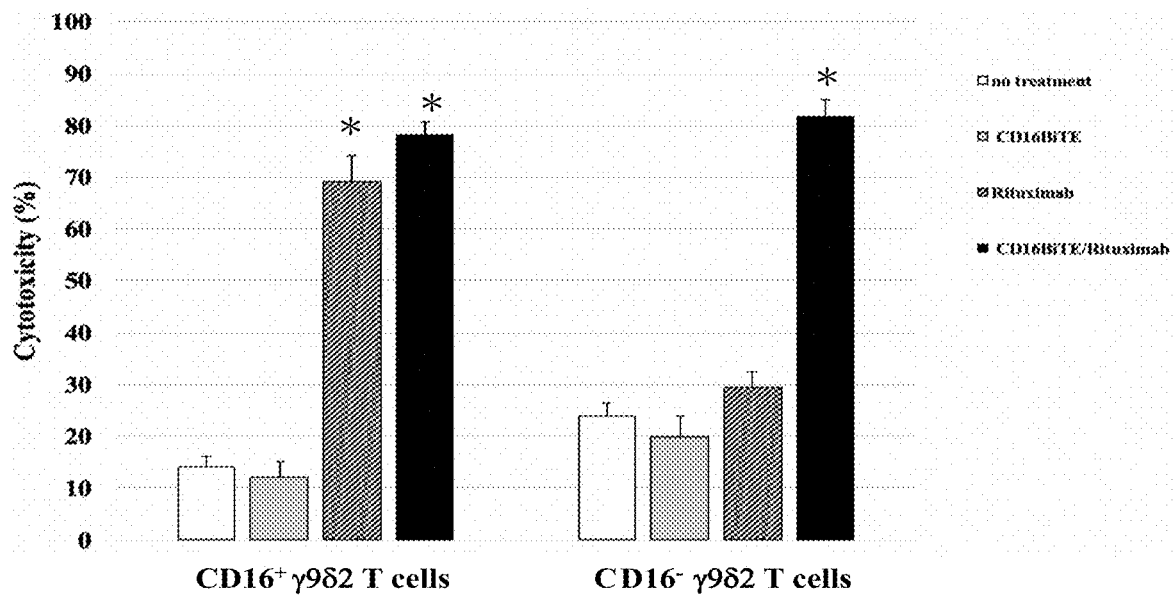

Results displayed in FIG. 7B show that rituximab-mediated Raji cell killing of CD16$^-$-γ9δ2 T cells in combination with the haCD16A-BiTE was comparable to that of CD16$^+$-γ9δ2 T cells, indicating that the functional activity of the haCD16A-BiTE is equivalent to that of high-affinity CD16 variants expressed on γ9δ2 T cells. *p<0.001, compared to the haCD16A-BiTE or rituximab alone for CD16$^-$-γ9δ2 T cells. *p<0.001, compared to the haCD16A-BiTE alone for CD16$^+$-γ9δ2 T cells.

Example 5

The Use of the haCD16A-BiTE to Deplete Unwanted Cells from T Cell Expansion Culture.

This example is to demonstrate the usefulness of the haCD16A-BiTE in depleting unwanted cells, such as tumor cells, from T cell expansion culture.

Written informed consent agreement were obtained from patients with chronic lymphocytic leukemia (CLL) and then peripheral blood samples were obtained. PBMC were isolated from 5 ml venous blood by density' gradient centrifugation using FICOLL® Paque PLUS (Sigma) according to the manufacturer's instruction. For the expansion of γ9δ2 T cells, PBMC (2×10$^6$ cells/ml) were stimulated with recombinant human IL2 (25 ng/ml; Prospec) and Zoledronate (1 uM; Sigma) for 14 days in RPMI-1640 medium containing 10% heat-inactivated FBS, penicillin (100 IU/ml), and streptomycin (100 μg/ml) at 37° C. in a humidified incubator with 5% $CO_2$. To deplete malignant B cells from these T cell expansion cultures, the haCD16A-BiTEs (80 ng/well) and rituximab (10 ug/well) were added to the cultures at day 10. Three days later, cultures were analyzed for malignant B cell death by flow cytometry analysis of both CD 19 marker (a marker for malignant B cell) and propidium iodide (PI) staining.

Figure 8:
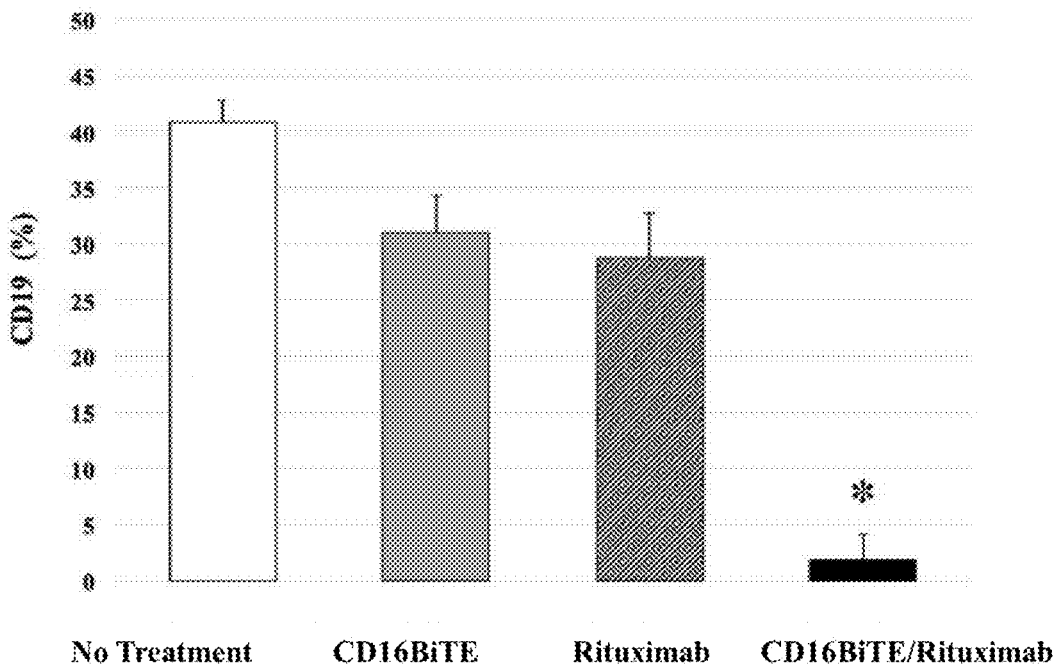
FIG. 8 shows the effect on depletion of malignant B cells from T cell expansion culture by treatment of said cell expansion culture with anti-CD20 antibodies (Rituximab) and the haCD16A-BiTEs.

FIG. 8 shows that CD19-positive cells decreased after treatment with the haCD16A-BiTEs and rituximab, demonstrating that the haCD16A-BiTE combined with rituximab has the ability to deplete malignant B cells from T cell expansion culture. *p<0.001, compared to the haCD16A-BiTE or rituximab alone.

Example 6

The Ability of the haCD16A-BiTE to Mediate Killing of EBV-Infected B Cells in the Presence of Anti-EBV IgG Antibodies and T Cells.

To establish the usefulness of the haCD16A-BiTE in viral disease treatment, EBV-infected B cell lines were used as model virally-infected cells to test the ability of the haCD16A-BiTE to mediate killing of EBV-infected B cells in the presence of anti-EBV IgG antibodies and T cells.

EBV is a gamma herpes virus that infects 90% of the population. EBV establishes life-long latency in memory B cells and oral epithelial cells. In the immune competent host, circulating EBV-specific cytotoxic T lymphocytes maintain EBV-infected B cells at a level of less than 1% of the B-cell pool. However, in the immunosuppressed host, uncontrolled proliferation of EBV-infected B cells contributes to lymphoproliferative disorders such as post-transplantation lymphoproliferative disorder (PTLD) after solid organ transplantation or hematopoietic stem cell transplantation. Moreover, a significant proportion of Hodgkin lymphomas, non-Hodgkin lymphomas, and nasopharyngeal carcinomas are associated with EBV infection. There are limited treatment options for EBV-related malignancies beyond standard chemotherapy and radiation. One promising modality is adoptive cell therapy using EBV-specific T cells, which has shown efficacy for PTLD (success in 70% of cases). Amore ideal therapeutic agent would be an antibody that can specifically recognize one of the more broadly expressed antigens: latent membrane protein-1 (LMP1) or LMP2 (Ahmed et al. JCI Insight, 3, e97805, (2018)).

Immortalized EBV-infected B cells express LMP1 and were used as target cells and jurkat T cells as negative control cells. Experiments were performed exactly as described in Example 2, except that a human anti-LMP1 IgG antibody (10 μg/well) (Creative Biolab) were used instead.

Figure 9:
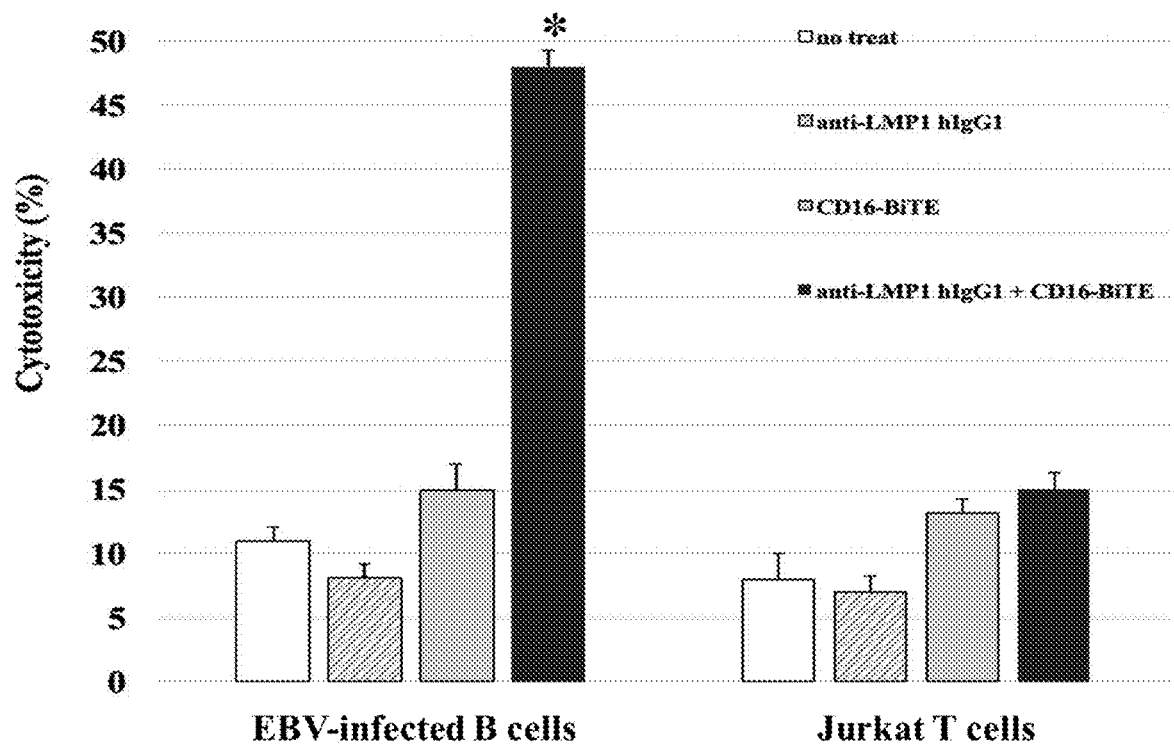
FIG. 9 shows the effect on killing of EBV-infected cell lines by treatment of said cell lines with anti-latent membrane protein 1 (LMP1) antibodies and the haCD16A-BiTEs alone or in combination in the presence of T cells.

FIG. 9 prove that in the presence of T cells, the haCD16A-BiTE exhibits a synergistic effect in killing EBV-infected B cells when combined with the anti-LMP1 IgG antibody, as compared to using the haCD16A-BiTE or anti-LMP1 antibody alone. *p<0.001, compared to the haCD16A-BiTE or anti-LMP1 antibody alone.

Example 7

In Vitro Activity Assay of the haCD16A-BiTE to Mediate Killing of PD-L1-Expressing Tumor Cells.

By overexpressing PD-L1, tumor cells exploit the PD-1/PD-L1 pathway to promote an immunosuppressive environment and allow tumor growth (Topalian et al., Curr Opin Immunol, 24, 207-212 (2012)). Hence, PD-L also is a tumor-associated antigen Blocking PD-L1 inhibitory signals with anti-PD-L1 IgG mAbs not only can restore T-cell anti-tumor activity, but also provide an opportunity to eradicate tumor cells by ADCC.

To examine the potential of the haCD16A-BiTE to endow T cells with ADCC activity to mediate eradication of PD-L1-expressing tumor cells by anti-PD-L1 IgG mAbs. We screened tumor cells for PD-L1-expression and carried out experiments exactly as described in Example 2, except that a PD-L1-expressing tumor cell line (A431) and a human anti-PD-L1 IgG antibody (10 μg/well)(Invivogen) were used instead. In this experiment, A431 cells were used as target cells. The MCF-7 cell line was PD-L1-low breast cancer cells.

Figure 10:
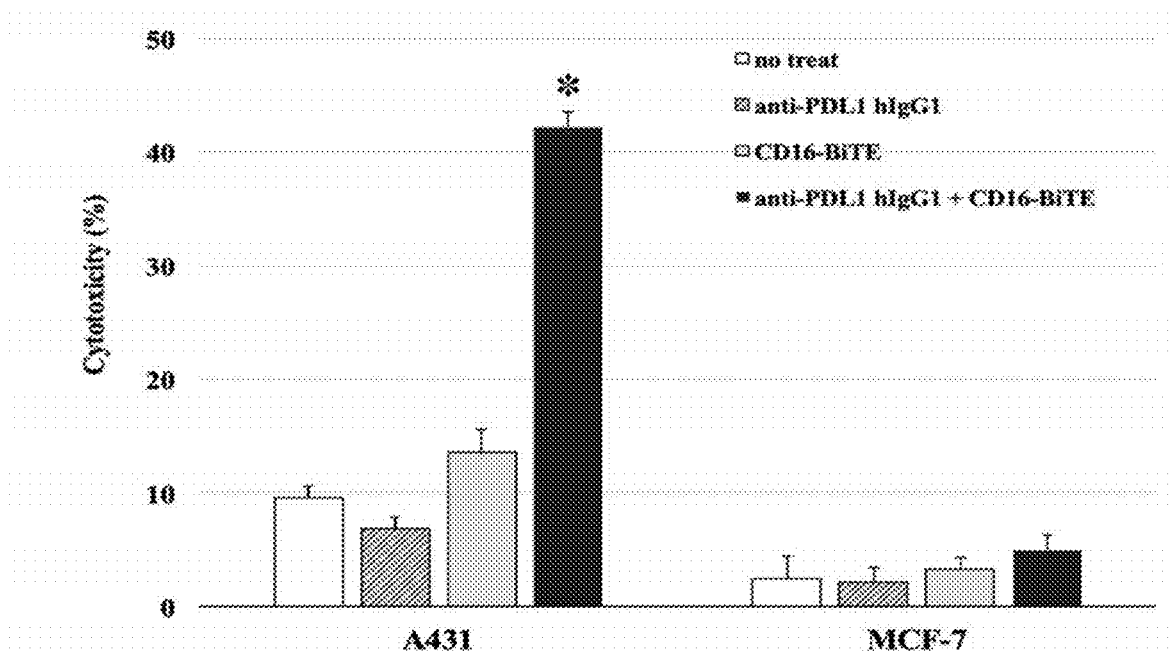
FIG. 10 shows the effect on killing of PD-L1-expressing cell line by treatment of said cell line with anti-PD-L1 antibodies and the haCD16A-BiTEs alone or in combination in the presence of T cells.

The results as shown in FIG. 10 prove that in the presence of T cells, the haCD16A-BiTE exhibits a synergistic effect in killing PD-L1-expressing cells (A431) when combined with an anti-PD-L1 IgG antibody, as compared to using the haCD16A-BiTE or anti-PD-L1 antibody alone. *p<0.001, compared to haCD16A-BiTE or anti-PD-L1 antibody alone.

Example 8

In Vivo Assay for the Activity of the haCD16A-BiTE on Killing of CD20-Expressing Tumor Cells in an Immunodeficient NOD Mouse Model.

Our invention to be effective in enhancing efficacy of therapeutic antibodies requires the coming together of four components to form a complex. These components include the tumor cell, the antibody, the haCD16A-BiTE, and the T cell. In vivo proof-of-concept studies were performed to demonstrate that this complex formation occurs in vivo, in addition to demonstrating the in vivo activity of the haCD16A-BiTE.

These experiments were carried out in T cells-lacking immunodeficient NOD.Cg-Prkdc$^{scid}$Il2rg$^{tm1Wjl}$/YckNarl (RMRC 13288) mice. First, the genes of luciferase and green fluorescent protein were transduced into Raji blood tumor cells using lentiviral vector (Zhou et al., Blood, 120, 4334-4342 (2012).) The Raji cells (1×10$^6$ cells) that express luciferase and green fluorescent protein were implanted into NOD mice via tail vein injection. On day 7 after the implantation of Raji cells, T cells obtained as described in Example 2 were implanted into the NOD mice via tail vein injection. The amount of T cells implanted per injection was 10-fold the amount of Raji cells. T cells were implanted once every 4 days for a total of 2 implantations. In addition, on day 7 after the implantation of Raji cells, the haCD16A-BiTE was infused via tail vein for 9 consecutive days with a daily dose of 800 ng, which was delivered by one bolus injection. Rituximab (10 mg/kg) was administered twice via tail vein on day 7 and 1 after Raji cell implantation. Mice of the control group received T cell implantation only.

Figure 11:
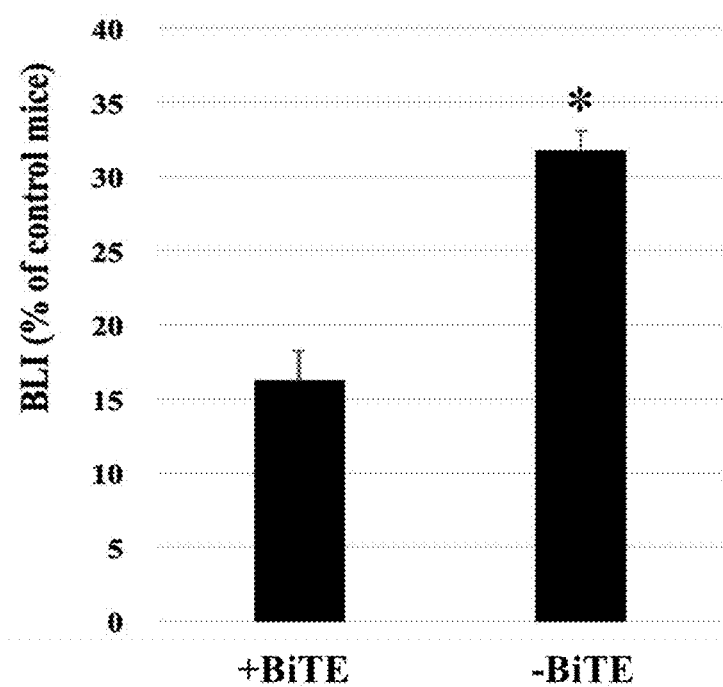
FIG. 11 shows, in the presence of T cells, the in vivo effect of the combination therapy with the haCD16A-BiTEs and rituximab, and rituximab monotherapy on reducing cancer cell growth.

The bioluminescence imaging (BLI) was conducted at different time points to monitor the clearance of Raji cells. At the end of the experiment, body weights in the treatment groups were comparable to those of the controls. The results in FIG. 11 show the BLI difference at the end of the experiment. Compared to mice treated with rituximab and T cells (without haCD16A-BiTE), the haCD16A-BiTE significantly enhanced Raji cell clearance by two-fold. Accordingly, tumor cell, antibody, the haCD16A-BiTE, and T cell can combine together as required for activity in vivo. More importantly, these data demonstrate the in vivo activity of to the haCD16A-BiTE. *p<0.01, compared to the haCD16A-BiTE, rituximab, and T cell combination.

Example 9

AAV-haCD16A-BiTE Mediates Peripheral Expression of the haCD16A-BITE in Mice.

To overcome the requirement of continuous infusion of BiTEs in therapeutic settings due to their short in vivo half-life, a AAV-mediated gene transfer approach was explored.

Mice (16 strain, male, 8-week old; n=5) were intraperitoneally injected with a viral vector of AAV-haCD16A-BiTE (FIG. 1A, $10^9$ vgc/animal; vgc: viral genome copy). Serum samples were collected from tail veins before (day 0) and after virus injection (day 2, 7, 14) and subjected to Western blot analysis to evaluate the protein levels of the haCD16A-BiTE. An HRP-conjugated polyclonal antibody was used to probe the 6×Histidine tag on the c-terminal of the haCD16A-BiTE. The levels of detected proteins were measured by densitometric analysis and presented as optical density values per ml of serum.

Figure 12:
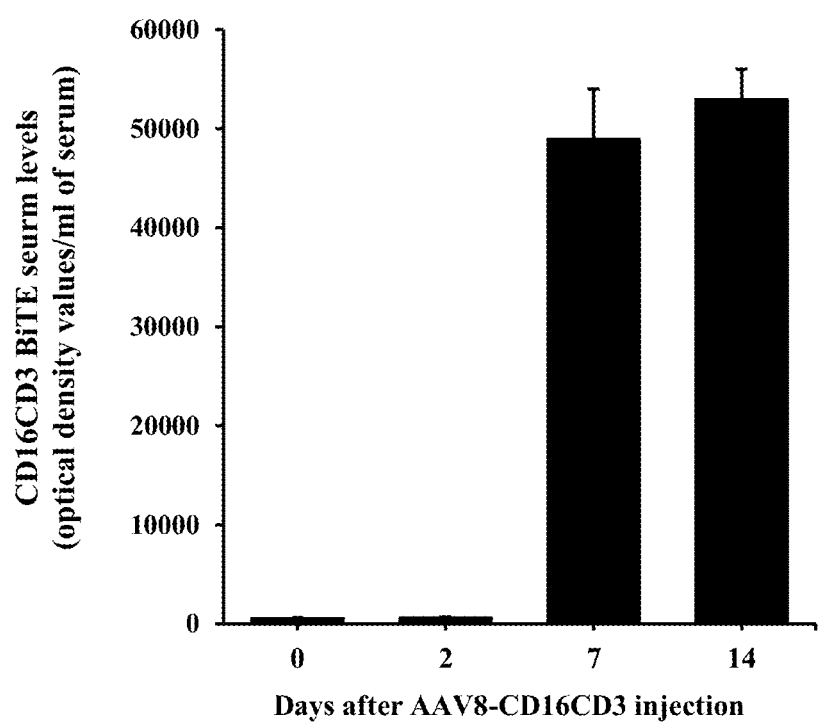
FIG. 12 shows the in vivo production of the haCD16A-BiTEs after AAV-mediated haCD16A-BiTE gene transfer.

The results in FIG. 12 show that 7 days after injecting with AAV-haCD16A-BiTE, the haCD16A-BiTE was detected in peripheral blood of mice and its presence lasts for at least 7 days. These results demonstrate that in vivo persistent production of the haCD16A-BiTE is achievable by in vivo virus-mediated haCD16A-BiTE gene transfer.

While the present invention has been described in conjunction with the specific embodiments set forth above, many alternatives thereto and modifications and variations thereof will be apparent to those of ordinary skill in the art. All such alternatives, modifications and variations are regarded as falling within the scope of the present invention.

What is claimed is:

1. An isolated fusion protein comprising:
   (a) an Fc-binding extracellular domain of human CD16A, wherein the Fc-binding extracellular domain of human CD16A has the amino acid sequence as set forth in SEQ ID NO: 2; and
   (b) an anti-human CD3 single-chain variable fragment that both specifically binds to human CD3 and activates human T cells;
   and wherein the C-terminal residue of SEQ ID NO: 2 is directly fused to the N-terminal residue of the anti-human CD3 single-chain variable fragment, wherein the anti-human CD3 single-chain variable fragment has the amino acid sequence as set forth in SEQ ID NO: 4.

2. The fusion protein of claim 1, which further comprises a protein purification tag, wherein the protein purification tag is a 6×Histidine tag.

3. An isolated polynucleotide encoding the fusion protein of claim 1, which comprises the nucleic acid sequence as set forth in SEQ ID NO: 7.

4. The polynucleotide of claim 3, which is contained in an adeno-associated virus vector.

5. An isolated host cell comprising the polynucleotide of claim 3.

6. The host cell of claim 5, wherein the polynucleotide is contained in an adeno-associated virus vector.

7. A method for inducing antibody-dependent cellular cytotoxicity directed against tumor cells or virally-infected cells in a subject having a tumor comprising said tumor cells or having said virally-infected cells, comprising administrating to the subject:
   (a) a pharmaceutical composition comprising an effective amount of the fusion protein according to claim 1 and optionally a pharmaceutically acceptable carrier or excipient; and
   (b) an antibody comprising a human IgG Fc domain, which specifically binds to an antigen on the surface of said tumor or virally-infected cells.

8. The method according to claim 7, wherein the pharmaceutical composition further comprises said antibody.

9. The fusion protein of claim 1, wherein the Fc-binding extracellular domain of human CD16A consists of the amino acid sequence of SEQ ID NO: 2 and/or the anti-human CD3 single-chain variable fragment consists of the amino acid sequence of SEQ ID NO: 4.

10. The method of claim 7, wherein said antibody specifically binds to a tumor antigen selected from CD20, EGFR, HER2, and PD-L1, or to an Epstein-Barr virus (EBV) antigen selected from LMP1 and LMP2.

11. A method for treating cancer or viral infection in a subject having cancer or viral infection by inducing antibody-dependent cellular cytotoxicity directed against the cancer cells or virally-infected cells in a subject, said method comprising administrating to the subject:
   (a) a pharmaceutical composition comprising a therapeutically effective amount of the fusion protein according to claim 1 and optionally a pharmaceutically acceptable carrier or excipient; and
   (b) an antibody comprising a human IgG Fc domain, which specifically binds to an antigen on the surface of said cancer or virally-infected cells.

12. The method according to claim 11, wherein the pharmaceutical composition further comprises said antibody.

13. The method of claim 11, wherein said antibody specifically binds to a tumor antigen selected from CD20, EGFR, HER2, and PD-L1, or to an Epstein-Barr virus (EBV) antigen selected from LMP1 and LMP2.

14. The method of claim 11, wherein said subject is human.

* * * * *

UNITED STATES PATENT AND TRADEMARK OFFICE
CERTIFICATE OF CORRECTION

| | | |
|---|---|---|
| PATENT NO. | : 12,269,863 B2 | Page 1 of 1 |
| APPLICATION NO. | : 17/057957 | |
| DATED | : April 8, 2025 | |
| INVENTOR(S) | : Hsin-Yi Huang, Cheng Hao Liao and Chun-Ming Lin | |

It is certified that error appears in the above-identified patent and that said Letters Patent is hereby corrected as shown below:

On the Title Page

Item (72)
The city name of inventor Chun-Ming Lin should be "Taipei", rather than "Taipey"

Signed and Sealed this
Fifteenth Day of July, 2025

Coke Morgan Stewart
*Acting Director of the United States Patent and Trademark Office*